(12) United States Patent
Takemori et al.

(10) Patent No.: US 11,339,224 B2
(45) Date of Patent: May 24, 2022

(54) ANTI-EVA1 PROTEIN ANTIBODY

(71) Applicant: NATIONAL UNIVERSITY CORPORATION HOKKAIDO UNIVERSITY, Sapporo (JP)

(72) Inventors: Toshitada Takemori, Wako (JP); Mikako Shirouzu, Wako (JP); Miho Tanaka, Wako (JP); Tamami Ueshima, Wako (JP); Toru Kondo, Wako (JP)

(73) Assignee: NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 316 days.

(21) Appl. No.: 15/748,875

(22) PCT Filed: Jul. 29, 2016

(86) PCT No.: PCT/JP2016/072348
§ 371 (c)(1),
(2) Date: Apr. 27, 2018

(87) PCT Pub. No.: WO2017/022668
PCT Pub. Date: Feb. 9, 2017

(65) Prior Publication Data
US 2019/0256610 A1 Aug. 22, 2019

(30) Foreign Application Priority Data
Jul. 31, 2015 (JP) .............................. JP2015-152941

(51) Int. Cl.
| | | |
|---|---|---|
| C07K 16/30 | (2006.01) | |
| C07K 16/28 | (2006.01) | |
| A61P 35/00 | (2006.01) | |
| A61K 39/395 | (2006.01) | |
| A61K 39/00 | (2006.01) | |

(52) U.S. Cl.
CPC ............ *C07K 16/30* (2013.01); *A61K 39/395* (2013.01); *A61P 35/00* (2018.01); *A61K 2039/505* (2013.01); *C07K 2317/21* (2013.01); *C07K 2317/24* (2013.01); *C07K 2317/52* (2013.01); *C07K 2317/565* (2013.01); *C07K 2317/732* (2013.01); *C07K 2319/00* (2013.01); *C07K 2319/01* (2013.01)

(58) Field of Classification Search
CPC .................................................... C07K 16/30
See application file for complete search history.

(56) References Cited

U.S. PATENT DOCUMENTS

2013/0224208 A1* 8/2013 Kondo ................ A61K 31/542
424/138.1

FOREIGN PATENT DOCUMENTS

| JP | 2013-203709 A | 10/2013 |
|---|---|---|
| WO | 2012/043747 A1 | 4/2012 |

OTHER PUBLICATIONS

Bendig M. M. (Methods: A Companion to Methods in Enzymology, 1995; 8:83-93) (Year: 1995).*
Portolano (The Journal of Immunology, vol. 150, No. 3, p. 880-887, 1993) (Year: 1993).*
Rudikoff et al. (Proceedings of the National Academy of Sciences USA, vol. 79, p. 1979-1983, 1982) (Year: 1982).*
Johnson and Wu (Methods in Molecular Biology, Antibody Engineering: Methods and Protocols, vol. 248, p. 11-25, 2004) (Year: 2004).*
Paul (Fundamental Immunology, 3rd Edition, 1993, pp. 292-295) (Year: 1993).*
Martin (UCL, http://www.bioinf.org.uk/abs/info.html#kabatnum, 2020) (Year: 2020).*
Nahir Garabatos et al., "A Monoclonal Antibody Against the Extracellular Domain of Mouse and Human Epithelial V-like Antigen 1 Reveals a Restricted Expression Pattern Among CD4- CD8- Thymocytes", Monoclonal Antibodies in Immunodiagnosis and Immunotherapy, 2014, pp. 305-311, vol. 33, No. 5.
International Preliminary Report on Patentability for PCT/JP2016/072348, dated Feb. 6, 2018.
Written Opinion for PCT/JP2016/072348, dated Oct. 25, 2016.
International Search Report for PCT/JP2016/072348, dated Oct. 25, 2016.
Communication, dated Feb. 21, 2019, issued by the European Patent Office in counterpart European Application No. 16832947.2.

* cited by examiner

*Primary Examiner* — Michael Allen
(74) *Attorney, Agent, or Firm* — Sughrue Mion, PLLC

(57) ABSTRACT

In order to provide an antibody having high therapeutic and prophylactic effects against cancer and the like, three types of mouse monoclonal antibodies were prepared which exhibit high affinities for a human-derived Eva1 protein. Moreover, constant regions of these antibodies were substituted with human-derived constant regions to also prepare chimeric antibodies. Further, these mouse antibodies and chimeric antibodies were found to have high ADCC and/or CDC activities. Furthermore, it was also revealed that administering these antibodies to mice having been subjected to melanoma cell administration suppresses the metastasis and the like of the cells to the lungs.

4 Claims, 23 Drawing Sheets

Specification includes a Sequence Listing.

CDRs of VH (B2E5-48)

CDR1           CDR2

QVQLQQPGAELVKPGASVKLSCKAS<u>GYTFTNY</u>WMHWVKLRPGQGFEWIGEI<u>NPTNGG</u>TDYNEKFK
RKATLTVDKSSSTAYMQLSSLTSEDSAVYYCTI<u>YTTALDY</u>WGQGTTLTVSS

CDR3

CDRs of VL (B2E5-48)

CDR1          CDR2

QIVLTQSPALMSASPGERVTLT<u>CSASSSVGYMY</u>WYQQKPGSSPKPWIY<u>VTSNLAS</u>GVPARFSGSGSGTS
YSLTISSMEAEDAATYYC<u>QQWSSNPPT</u>FGAGTKLELK

CDR3

CDRs of VH (C3)

CDR1           CDR2

EVKLVESGGGLVQPGGSLKLSCAAS<u>GFTFSSY</u>TMSWVRQTPEKRLEWVAYI<u>TTGAGR</u>TYYPDTV
KGRFTISRDNAKNTLYLQMSSLKSEDTAMYYCAR<u>HRGDY</u>WGQGTSVTVSSA

CDR3

CDRs of VL (C3)

CDR1          CDR2

SIVMTQTPKFLLVSAGDRVTITC<u>KASQSVSNDVA</u>WYQQKPGQSPKLLIY<u>YASNRFT</u>GVPDRFTGSG
YGTDFTFTISTVQAEDLAVYFC<u>QQDYSSPWT</u>FGGGTKLEIK

CDR3

Fig. 3

CDRs of VH (A5D11-10)

CDR1                               CDR2
EVQLKESGPGLVQPSQSLSITCTVSGFSLTRYGVHWVRQSPGKGLEWLGVIWSGGSTDYNAAFIS
RLSISKDNSKSQVFFKMNSLQANDTAIYYCARNGYDGGYAMDYWGQGTSVTVSS
                                                                       CDR3

CDRs of VL (A5D11-10)

CDR1                                    CDR2
DIQMTQTTSSLSASLGDRVTISCRASQDISNYLNWYQQKPDGTVKLLIYYTSRLHSGVPSRFSGSGS
RIDYSLTISNLEQEDFATYFCQQSDTLPPWTFGGGTKLEIK
                           CDR3

SEQUENCE LISTING

<160> NUMBER OF SEQ ID NOS: 38

<210> SEQ ID NO 1
<211> LENGTH: 384
<212> TYPE: DNA

<213> ORGANISM: Mus musculus
<220> FEATURE:
<221> NAME/KEY: CDS
<222> LOCATION: (1)..(384)
<223> OTHER INFORMATION: Signal peptide and Variable Region of Light
      Chain (B2E5-48)

<400> SEQUENCE: 1

```
atg gat ttt caa gtg cag att ttc agc ttc ctg cta atg agt gcc tca       48
Met Asp Phe Gln Val Gln Ile Phe Ser Phe Leu Leu Met Ser Ala Ser
1               5                   10                  15 gtc ata atg tcc agg gga caa att gtt ctc acc cag tct cca gca ctc       96
Val Ile Met Ser Arg Gly Gln Ile Val Leu Thr Gln Ser Pro Ala Leu
                20                  25                  30 atg tct gca tct cca ggg gag agg gtc acc ttg acc tgc agt gcc agc      144
Met Ser Ala Ser Pro Gly Glu Arg Val Thr Leu Thr Cys Ser Ala Ser
            35                  40                  45 tca agt gta ggt tac atg tac tgg tac cag cag aag cca gga tcc tcc      192
Ser Ser Val Gly Tyr Met Tyr Trp Tyr Gln Gln Lys Pro Gly Ser Ser
        50                  55                  60 ccc aaa ccc tgg att tat gtc aca tcc aac ctg gct tct gga gtc cct      240
Pro Lys Pro Trp Ile Tyr Val Thr Ser Asn Leu Ala Ser Gly Val Pro
65                  70                  75                  80 gct cgc ttc agt ggc agt ggg tct ggg acc tct tac tct ctc aca atc      288
Ala Arg Phe Ser Gly Ser Gly Ser Gly Thr Ser Tyr Ser Leu Thr Ile
                85                  90                  95 agc agc atg gag gct gaa gat gct gcc act tat tac tgc cag cag tgg      336
Ser Ser Met Glu Ala Glu Asp Ala Ala Thr Tyr Tyr Cys Gln Gln Trp
                100                 105                 110 agt agt aac cca cct acg ttc ggt gct ggg acc aag ctg gag ctg aaa      384
Ser Ser Asn Pro Pro Thr Phe Gly Ala Gly Thr Lys Leu Glu Leu Lys
            115                 120                 125
```

<210> SEQ ID NO 2
<211> LENGTH: 128
<212> TYPE: PRT
<213> ORGANISM: Mus musculus

<400> SEQUENCE: 2

```
Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
                20                  25                  30

Met Ser Ala Ser Pro Gly Glu Arg Val Thr Leu Thr Cys Ser Ala Ser
            35                  40                  45

Ser Ser Val Gly Tyr Met Tyr Trp Tyr Gln Gln Lys Pro Gly Ser Ser
        50                  55                  60

Pro Lys Pro Trp Ile Tyr Val Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
                100                 105                 110

Ser Ser Asn Pro Pro Thr Phe Gly Ala Gly Thr Lys Leu Glu Leu Lys
            115                 120                 125
```

<210> SEQ ID NO 3
<211> LENGTH: 106
<212> TYPE: PRT
<213> ORGANISM: Mus musculus
<220> FEATURE:

```
<221> NAME/KEY: SITE
<222> LOCATION: (1)..(106)
<223> OTHER INFORMATION: Variable Region of Light Chain (B2E5-48)

<400> SEQUENCE: 3

Gln Ile Val Leu Thr Gln Ser Pro Ala Leu Met Ser Ala Ser Pro Gly
1               5                   10                  15

Glu Arg Val Thr Leu Thr Cys Ser Ala Ser Ser Ser Val Gly Tyr Met
            20                  25                  30

Tyr Trp Tyr Gln Gln Lys Pro Gly Ser Ser Pro Lys Pro Trp Ile Tyr
        35                  40                  45

Val Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105

<210> SEQ ID NO 4
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR1 of Light Chain (B2E5-48)

<400> SEQUENCE: 4

Ser Ala Ser Ser Ser Val Gly Tyr Met Tyr
1               5                   10

<210> SEQ ID NO 5
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain (B2E5-48)

<400> SEQUENCE: 5

Val Thr Ser Asn Leu Ala Ser
1               5

<210> SEQ ID NO 6
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Light Chain (B2E5-48)

<400> SEQUENCE: 6

Gln Gln Trp Ser Ser Asn Pro Pro Thr
1               5

<210> SEQ ID NO 7
<211> LENGTH: 405
<212> TYPE: DNA
<213> ORGANISM: Mus musculus
<220> FEATURE:
<221> NAME/KEY: CDS
```

<222> LOCATION: (1)..(405)
<223> OTHER INFORMATION: Signal peptide and Variable Region of Heavy
      Chain (B2E5-48)

<400> SEQUENCE: 7

```
atg gga tgg agc tac atc att ttc ttt ttg gta gca aca gct aca ggt      48
Met Gly Trp Ser Tyr Ile Ile Phe Phe Leu Val Ala Thr Ala Thr Gly
1               5                   10                  15 gtc cac tcc cag gtc caa ctc cag cag cct ggg gct gaa ctg gtg aag      96
Val His Ser Gln Val Gln Leu Gln Gln Pro Gly Ala Glu Leu Val Lys
            20                  25                  30 cct ggg gct tca gtg aag ttg tcc tgc aag gct tct ggc tac acc ttc     144
Pro Gly Ala Ser Val Lys Leu Ser Cys Lys Ala Ser Gly Tyr Thr Phe
        35                  40                  45 acc aac tac tgg atg cac tgg gtg aag ctg agg cct gga caa ggc ttt     192
Thr Asn Tyr Trp Met His Trp Val Lys Leu Arg Pro Gly Gln Gly Phe
    50                  55                  60 gag tgg att gga gag att aat cct acc aat ggt ggt act gac tac aat     240
Glu Trp Ile Gly Glu Ile Asn Pro Thr Asn Gly Gly Thr Asp Tyr Asn
65                  70                  75                  80 gag aag ttc aag aga aag gcc aca ctg act gta gac aaa tcc tcc agc     288
Glu Lys Phe Lys Arg Lys Ala Thr Leu Thr Val Asp Lys Ser Ser Ser
                85                  90                  95 aca gcc tac atg caa ctc agc agc ctg aca tct gag gac tct gcg gtc     336
Thr Ala Tyr Met Gln Leu Ser Ser Leu Thr Ser Glu Asp Ser Ala Val
            100                 105                 110 tat tac tgc aca ata tat act acg gct ctt gac tac tgg ggc caa ggc     384
Tyr Tyr Cys Thr Ile Tyr Thr Thr Ala Leu Asp Tyr Trp Gly Gln Gly
        115                 120                 125 acc act ctc aca gtc tcc tca                                          405
Thr Thr Leu Thr Val Ser Ser
    130                 135
```

<210> SEQ ID NO 8
<211> LENGTH: 135
<212> TYPE: PRT
<213> ORGANISM: Mus musculus

<400> SEQUENCE: 8

```
Met Gly Trp Ser Tyr Ile Ile Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Met His Trp Val Lys Leu Arg Pro Gly Gln Gly Phe
    50                  55                  60

Glu Trp Ile Gly Glu Ile Asn Pro Thr Asn Gly Gly Thr Asp Tyr Asn
65                  70                  75                  80

Glu Lys Phe Lys Arg Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Ile Tyr Thr Thr Ala Leu Asp Tyr Trp Gly Gln Gly
        115                 120                 125

Thr Thr Leu Thr Val Ser Ser
    130                 135
```

<210> SEQ ID NO 9

```
<211> LENGTH: 116
<212> TYPE: PRT
<213> ORGANISM: Mus musculus
<220> FEATURE:
<221> NAME/KEY: SITE
<222> LOCATION: (1)..(116)
<223> OTHER INFORMATION: Variable Region of Heavy Chain (B2E5-48)

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Leu Arg Pro Gly Gln Gly Phe Glu Trp Ile
        35                  40                  45

Gly Glu Ile Asn Pro Thr Asn Gly Gly Thr Asp Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Tyr Thr Thr Ala Leu Asp Tyr Trp Gly Gln Gly Thr Thr Leu
            100                 105                 110

Thr Val Ser Ser
        115

<210> SEQ ID NO 10
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR1 of Heavy Chain (B2E5-48)

<400> SEQUENCE: 10

Gly Tyr Thr Phe Thr Asn Tyr
1               5

<210> SEQ ID NO 11
<211> LENGTH: 6
<212> TYPE: PRT
<213> ORGANISM: Mus musculus
<220> FEATURE:
<221> NAME/KEY: SITE
<222> LOCATION: (1)..(6)
<223> OTHER INFORMATION: CDR2 of Heavy Chain (B2E5-48)

<400> SEQUENCE: 11

Asn Pro Thr Asn Gly Gly
1               5

<210> SEQ ID NO 12
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR3 of Heavy Chain (B2E5-48)

<400> SEQUENCE: 12

Tyr Thr Thr Ala Leu Asp Tyr
1               5
```

<210> SEQ ID NO 13
<211> LENGTH: 381
<212> TYPE: DNA
<213> ORGANISM: Mus musculus
<220> FEATURE:
<221> NAME/KEY: CDS
<222> LOCATION: (1)..(381)
<223> OTHER INFORMATION: Signal peptide and Variable Region of Light
      Chain (C3)

<400> SEQUENCE: 13

```
atg aag tca cag acc cag gtc ttc gta ttt cta ctg ctc tgt gtg tct        48
Met Lys Ser Gln Thr Gln Val Phe Val Phe Leu Leu Leu Cys Val Ser
1               5                   10                  15 ggt gct cat ggg agt att gtg atg acc cag act ccc aaa ttc ctg ctt        96
Gly Ala His Gly Ser Ile Val Met Thr Gln Thr Pro Lys Phe Leu Leu
            20                  25                  30 gta tca gca gga gac agg gtt acc ata acc tgc aag gcc agt cag agt       144
Val Ser Ala Gly Asp Arg Val Thr Ile Thr Cys Lys Ala Ser Gln Ser
        35                  40                  45 gtg agt aat gat gta gct tgg tac caa cag aag cca ggg cag tct cct       192
Val Ser Asn Asp Val Ala Trp Tyr Gln Gln Lys Pro Gly Gln Ser Pro
    50                  55                  60 aaa ctg ctg ata tac tat gca tcc aat cgc tac act gga gtc cct gat       240
Lys Leu Leu Ile Tyr Tyr Ala Ser Asn Arg Tyr Thr Gly Val Pro Asp
65                  70                  75                  80 cgc ttc act ggc agt gga tat ggg acg gat ttc act ttc acc atc agc       288
Arg Phe Thr Gly Ser Gly Tyr Gly Thr Asp Phe Thr Phe Thr Ile Ser
                85                  90                  95 act gtg cag gct gaa gac ctg gca gtt tat ttc tgt cag cag gat tat       336
Thr Val Gln Ala Glu Asp Leu Ala Val Tyr Phe Cys Gln Gln Asp Tyr
            100                 105                 110 agc tct ccg tgg acg ttc ggt gga ggc acc aag ctg gaa atc aaa           381
Ser Ser Pro Trp Thr Phe Gly Gly Gly Thr Lys Leu Glu Ile Lys
        115                 120                 125
```

<210> SEQ ID NO 14
<211> LENGTH: 127
<212> TYPE: PRT
<213> ORGANISM: Mus musculus

<400> SEQUENCE: 14

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Trp Thr Phe Gly Gly Gly Thr Lys Leu Glu Ile Lys
        115                 120                 125
```

<210> SEQ ID NO 15

```
<211> LENGTH: 107
<212> TYPE: PRT
<213> ORGANISM: Mus musculus
<220> FEATURE:
<221> NAME/KEY: SITE
<222> LOCATION: (1)..(107)
<223> OTHER INFORMATION: Variable Region of Light Chain (C3)

<400> SEQUENCE: 15

Ser Ile Val Met Thr Gln Thr Pro Lys Phe Leu Leu Val Ser Ala Gly
1               5                  10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Phe Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 16
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: CDR1 of Light Chain (C3)

<400> SEQUENCE: 16

Lys Ala Ser Gln Ser Val Ser Asn Asp Val Ala
1               5                  10

<210> SEQ ID NO 17
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain (C3)

<400> SEQUENCE: 17

Tyr Ala Ser Asn Arg Phe Thr
1               5

<210> SEQ ID NO 18
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Light Chain (C3)

<400> SEQUENCE: 18

Gln Gln Asp Tyr Ser Ser Pro Trp Thr
1               5

<210> SEQ ID NO 19
<211> LENGTH: 402
```

```
<212> TYPE: DNA
<213> ORGANISM: Mus musculus
<220> FEATURE:
<221> NAME/KEY: CDS
<222> LOCATION: (1)..(402)
<223> OTHER INFORMATION: Signal peptide and Variable Region of Heavy
      Chain (C3)

<400> SEQUENCE: 19 atg aat ttc ggg ctc agc ttg att ttc ctt gtc ctt gtt tta aaa ggt      48
Met Asn Phe Gly Leu Ser Leu Ile Phe Leu Val Leu Val Leu Lys Gly
1               5                   10                  15 gtc ctg tgt gaa gtg aaa ctg gtg gag tct ggg gga ggt tta gtg cag      96
Val Leu Cys Glu Val Lys Leu Val Glu Ser Gly Gly Gly Leu Val Gln
            20                  25                  30 cct gga ggg tcc ctg aaa ctc tcc tgt gca gcc tct gga ttc act ttc     144
Pro Gly Gly Ser Leu Lys Leu Ser Cys Ala Ala Ser Gly Phe Thr Phe
        35                  40                  45 agt agc tat acc atg tct tgg gtt cgc cag act cca gag aag agg ctg     192
Ser Ser Tyr Thr Met Ser Trp Val Arg Gln Thr Pro Glu Lys Arg Leu
    50                  55                  60 gag tgg gtc gca tac att act act ggt gct ggt agg acc tac tat cca     240
Glu Trp Val Ala Tyr Ile Thr Thr Gly Ala Gly Arg Thr Tyr Tyr Pro
65                  70                  75                  80 gac act gta aag ggc cga ttc acc atc tcc aga gac aat gcc aag aac     288
Asp Thr Val Lys Gly Arg Phe Thr Ile Ser Arg Asp Asn Ala Lys Asn
                85                  90                  95 acc ctg tac ctg caa atg agt agt ctg aag tct gag gac acg gcc atg     336
Thr Leu Tyr Leu Gln Met Ser Ser Leu Lys Ser Glu Asp Thr Ala Met
            100                 105                 110 tat tac tgt gca aga cat cgg ggg gac tac tgg ggt caa gga acc tca     384
Tyr Tyr Cys Ala Arg His Arg Gly Asp Tyr Trp Gly Gln Gly Thr Ser
        115                 120                 125 gtc acc gtc tcc tca gcc                                             402
Val Thr Val Ser Ser Ala
    130

<210> SEQ ID NO 20
<211> LENGTH: 134
<212> TYPE: PRT
<213> ORGANISM: Mus musculus

<400> SEQUENCE: 20

Met Asn Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Trp Val Ala Tyr Ile Thr Thr Gly Ala Gly Arg Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Arg Gly Asp Tyr Trp Gly Gln Gly Thr Ser
        115                 120                 125

Val Thr Val Ser Ser Ala
    130
```

<210> SEQ ID NO 21
<211> LENGTH: 115
<212> TYPE: PRT
<213> ORGANISM: Mus musculus
<220> FEATURE:
<221> NAME/KEY: SITE
<222> LOCATION: (1)..(115)
<223> OTHER INFORMATION: Variable Region of Heavy Chain (C3)

<400> SEQUENCE: 21

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Thr Thr Gly Ala Gly Arg Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Arg Gly Asp Tyr Trp Gly Gln Gly Thr Ser Val Thr Val
            100                 105                 110

Ser Ser Ala
        115

<210> SEQ ID NO 22
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR1 of Heavy Chain (C3)

<400> SEQUENCE: 22

Gly Phe Thr Phe Ser Ser Tyr
1               5

<210> SEQ ID NO 23
<211> LENGTH: 6
<212> TYPE: PRT
<213> ORGANISM: Mus musculus
<220> FEATURE:
<221> NAME/KEY: SITE
<222> LOCATION: (1)..(6)
<223> OTHER INFORMATION: CDR2 of Heavy Chain (C3)

<400> SEQUENCE: 23

Thr Thr Gly Ala Gly Arg
1               5

<210> SEQ ID NO 24
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR3 of Heavy Chain (C3)

<400> SEQUENCE: 24

His Arg Gly Asp Tyr
1               5

<210> SEQ ID NO 25
<211> LENGTH: 324
<212> TYPE: DNA
<213> ORGANISM: Mus musculus
<220> FEATURE:
<221> NAME/KEY: CDS
<222> LOCATION: (1)..(324)
<223> OTHER INFORMATION: Variable Region of Light Chain (A5D11-10)

<400> SEQUENCE: 25

```
gat atc cag atg aca cag act aca tct tcc ctg tct gcc tct ctg gga      48
Asp Ile Gln Met Thr Gln Thr Thr Ser Ser Leu Ser Ala Ser Leu Gly
1               5                   10                  15 gac aga gtc acc atc agt tgc agg gca agt cag gac att agc aat tat      96
Asp Arg Val Thr Ile Ser Cys Arg Ala Ser Gln Asp Ile Ser Asn Tyr
            20                  25                  30 tta aac tgg tat cag cag aaa cca gat gga act gtt aaa ctc ctt atc     144
Leu Asn Trp Tyr Gln Gln Lys Pro Asp Gly Thr Val Lys Leu Leu Ile
        35                  40                  45 tac tac aca tca aga tta cac tca gga gtc cca tca agg ttc agt ggc     192
Tyr Tyr Thr Ser Arg Leu His Ser Gly Val Pro Ser Arg Phe Ser Gly
    50                  55                  60 agt ggg tct cga ata gat tat tct ctc acc att agc aac ctg gag caa     240
Ser Gly Ser Arg Ile Asp Tyr Ser Leu Thr Ile Ser Asn Leu Glu Gln
65                  70                  75                  80 gaa gat ttt gcc act tac ttt tgc caa cag agt gat acg ctt cct ccg     288
Glu Asp Phe Ala Thr Tyr Phe Cys Gln Gln Ser Asp Thr Leu Pro Pro
                85                  90                  95 tgg acg ttc ggt gga ggc acc aag ctg gaa atc aaa                     324
Trp Thr Phe Gly Gly Gly Thr Lys Leu Glu Ile Lys
            100                 105
```

<210> SEQ ID NO 26
<211> LENGTH: 108
<212> TYPE: PRT
<213> ORGANISM: Mus musculus

<400> SEQUENCE: 26

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Arg Ile Asp Tyr Ser Leu Thr Ile Ser Asn Leu Glu Gln
65                  70                  75                  80

Glu Asp Phe Ala Thr Tyr Phe Cys Gln Gln Ser Asp Thr Leu Pro Pro
                85                  90                  95

Trp Thr Phe Gly Gly Gly Thr Lys Leu Glu Ile Lys
            100                 105

<210> SEQ ID NO 27
<211> LENGTH: 11
<212> TYPE: PRT
<213> ORGANISM: Mus musculus
<220> FEATURE:

```
<221> NAME/KEY: SITE
<222> LOCATION: (1)..(11)
<223> OTHER INFORMATION: CDR1 of Light Chain (A5D11-10)

<400> SEQUENCE: 27

Arg Ala Ser Gln Asp Ile Ser Asn Tyr Leu Asn
1               5                   10

<210> SEQ ID NO 28
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain (A5D11-10)

<400> SEQUENCE: 28

Tyr Thr Ser Arg Leu His Ser
1               5

<210> SEQ ID NO 29
<211> LENGTH: 10
<212> TYPE: PRT
<213> ORGANISM: Mus musculus
<220> FEATURE:
<221> NAME/KEY: SITE
<222> LOCATION: (1)..(10)
<223> OTHER INFORMATION: CDR3 of Light Chain (A5D11-10)

<400> SEQUENCE: 29

Gln Gln Ser Asp Thr Leu Pro Pro Trp Thr
1               5                   10

<210> SEQ ID NO 30
<211> LENGTH: 357
<212> TYPE: DNA
<213> ORGANISM: Mus musculus
<220> FEATURE:
<221> NAME/KEY: CDS
<222> LOCATION: (1)..(357)
<223> OTHER INFORMATION: Variable Region of Heavy Chain (A5D11-10)

<400> SEQUENCE: 30 gag gtg cag ctg aag gag tca gga cct ggc cta gtg cag ccc tca cag      48
Glu Val Gln Leu Lys Glu Ser Gly Pro Gly Leu Val Gln Pro Ser Gln
1               5                   10                  15 agc ctg tcc atc acc tgc aca gtc tct ggt ttc tca tta act agg tat      96
Ser Leu Ser Ile Thr Cys Thr Val Ser Gly Phe Ser Leu Thr Arg Tyr
            20                  25                  30 ggt gta cac tgg gtt cgc cag tct cca gga aag ggt ctg gag tgg ctg     144
Gly Val His Trp Val Arg Gln Ser Pro Gly Lys Gly Leu Glu Trp Leu
        35                  40                  45 gga gtg ata tgg agt ggt gga agc aca gac tat aat gca gct ttc ata     192
Gly Val Ile Trp Ser Gly Gly Ser Thr Asp Tyr Asn Ala Ala Phe Ile
    50                  55                  60 tcc aga ctg agc atc agc aag gac aat tcc aag agc caa gtt ttc ttt     240
Ser Arg Leu Ser Ile Ser Lys Asp Asn Ser Lys Ser Gln Val Phe Phe
65                  70                  75                  80 aaa atg aac agt ctg caa gct aat gac aca gcc ata tat tac tgt gcc     288
Lys Met Asn Ser Leu Gln Ala Asn Asp Thr Ala Ile Tyr Tyr Cys Ala
                85                  90                  95 aga aat ggt tac gac ggg ggc tat gct atg gac tac tgg ggt caa gga     336
Arg Asn Gly Tyr Asp Gly Gly Tyr Ala Met Asp Tyr Trp Gly Gln Gly
            100                 105                 110
```

```
acc tca gtc acc gtc tcc tca                                    357
Thr Ser Val Thr Val Ser Ser
        115
```

<210> SEQ ID NO 31
<211> LENGTH: 119
<212> TYPE: PRT
<213> ORGANISM: Mus musculus

<400> SEQUENCE: 31

Glu Val Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Arg Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Gly Tyr Asp Gly Gly Tyr Ala Met Asp Tyr Trp Gly Gln Gly
            100                 105                 110

Thr Ser Val Thr Val Ser Ser
        115

<210> SEQ ID NO 32
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR1 of Heavy Chain (A5D11-10)

<400> SEQUENCE: 32

Gly Phe Ser Leu Thr Arg Tyr
1               5

<210> SEQ ID NO 33
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR2 of Heavy Chain (A5D11-10)

<400> SEQUENCE: 33

Trp Ser Gly Gly Ser
1               5

<210> SEQ ID NO 34
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: CDR3 of Heavy Chain (A5D11-10)

<400> SEQUENCE: 34

Asn Gly Tyr Asp Gly Gly Tyr Ala Met Asp Tyr

<210> SEQ ID NO 35
<211> LENGTH: 648
<212> TYPE: DNA
<213> ORGANISM: Homo sapiens
<220> FEATURE:
<221> NAME/KEY: CDS
<222> LOCATION: (1)..(648)
<223> OTHER INFORMATION: hEva1

<400> SEQUENCE: 35

| | | | | | | | | | | | | | | | | |
|---|---|---|---|---|---|---|---|---|---|---|---|---|---|---|---|---|
| atg | tat | ggc | aag | agc | tct | act | cgt | gcg | gtg | ctt | ctt | ctc | ctt | ggc | ata | 48 |
| Met | Tyr | Gly | Lys | Ser | Ser | Thr | Arg | Ala | Val | Leu | Leu | Leu | Leu | Gly | Ile | |
| 1 | | | | 5 | | | | | 10 | | | | | 15 | | |

| cag | ctc | aca | gct | ctt | tgg | cct | ata | gca | gct | gtg | gaa | att | tat | acc | tcc | 96 |
|---|---|---|---|---|---|---|---|---|---|---|---|---|---|---|---|---|
| Gln | Leu | Thr | Ala | Leu | Trp | Pro | Ile | Ala | Ala | Val | Glu | Ile | Tyr | Thr | Ser | |
| | | 20 | | | | | 25 | | | | | 30 | | | | |

| cgg | gtg | ctg | gag | gct | gtt | aat | ggg | aca | gat | gct | cgg | tta | aaa | tgc | act | 144 |
|---|---|---|---|---|---|---|---|---|---|---|---|---|---|---|---|---|
| Arg | Val | Leu | Glu | Ala | Val | Asn | Gly | Thr | Asp | Ala | Arg | Leu | Lys | Cys | Thr | |
| | 35 | | | | | 40 | | | | | 45 | | | | | |

| ttc | tcc | agc | ttt | gcc | cct | gtg | ggt | gat | gct | cta | aca | gtg | acc | tgg | aat | 192 |
|---|---|---|---|---|---|---|---|---|---|---|---|---|---|---|---|---|
| Phe | Ser | Ser | Phe | Ala | Pro | Val | Gly | Asp | Ala | Leu | Thr | Val | Thr | Trp | Asn | |
| 50 | | | | | 55 | | | | | 60 | | | | | | |

| ttt | cgt | cct | cta | gac | ggg | gga | cct | gag | cag | ttt | gta | ttc | tac | tac | cac | 240 |
|---|---|---|---|---|---|---|---|---|---|---|---|---|---|---|---|---|
| Phe | Arg | Pro | Leu | Asp | Gly | Gly | Pro | Glu | Gln | Phe | Val | Phe | Tyr | Tyr | His | |
| 65 | | | | | 70 | | | | | 75 | | | | | 80 | |

| ata | gat | ccc | ttc | caa | ccc | atg | agt | ggg | cgg | ttt | aag | gac | cgg | gtg | tct | 288 |
|---|---|---|---|---|---|---|---|---|---|---|---|---|---|---|---|---|
| Ile | Asp | Pro | Phe | Gln | Pro | Met | Ser | Gly | Arg | Phe | Lys | Asp | Arg | Val | Ser | |
| | | | | 85 | | | | | 90 | | | | | 95 | | |

| tgg | gat | ggg | aat | cct | gag | cgg | tac | gat | gcc | tcc | atc | ctt | ctc | tgg | aaa | 336 |
|---|---|---|---|---|---|---|---|---|---|---|---|---|---|---|---|---|
| Trp | Asp | Gly | Asn | Pro | Glu | Arg | Tyr | Asp | Ala | Ser | Ile | Leu | Leu | Trp | Lys | |
| | | | 100 | | | | | 105 | | | | | 110 | | | |

| ctg | cag | ttc | gac | gac | aat | ggg | aca | tac | acc | tgc | cag | gtg | aag | aac | cca | 384 |
|---|---|---|---|---|---|---|---|---|---|---|---|---|---|---|---|---|
| Leu | Gln | Phe | Asp | Asp | Asn | Gly | Thr | Tyr | Thr | Cys | Gln | Val | Lys | Asn | Pro | |
| | | 115 | | | | | 120 | | | | | 125 | | | | |

| cct | gat | gtt | gat | ggg | gtg | ata | ggg | gag | atc | cgg | ctc | agc | gtc | gtg | cac | 432 |
|---|---|---|---|---|---|---|---|---|---|---|---|---|---|---|---|---|
| Pro | Asp | Val | Asp | Gly | Val | Ile | Gly | Glu | Ile | Arg | Leu | Ser | Val | Val | His | |
| | 130 | | | | | 135 | | | | | 140 | | | | | |

| act | gta | cgc | ttc | tct | gag | atc | cac | ttc | ctg | gct | ctg | gcc | att | ggc | tct | 480 |
|---|---|---|---|---|---|---|---|---|---|---|---|---|---|---|---|---|
| Thr | Val | Arg | Phe | Ser | Glu | Ile | His | Phe | Leu | Ala | Leu | Ala | Ile | Gly | Ser | |
| 145 | | | | | 150 | | | | | 155 | | | | | 160 | |

| gcc | tgt | gca | ctg | atg | atc | ata | ata | gta | att | gta | gtg | gtc | ctc | ttc | cag | 528 |
|---|---|---|---|---|---|---|---|---|---|---|---|---|---|---|---|---|
| Ala | Cys | Ala | Leu | Met | Ile | Ile | Ile | Val | Ile | Val | Val | Val | Leu | Phe | Gln | |
| | | | | 165 | | | | | 170 | | | | | 175 | | |

| cat | tac | cgg | aaa | aag | cga | tgg | gcc | gaa | aga | gct | cat | aaa | gtg | gtg | gag | 576 |
|---|---|---|---|---|---|---|---|---|---|---|---|---|---|---|---|---|
| His | Tyr | Arg | Lys | Lys | Arg | Trp | Ala | Glu | Arg | Ala | His | Lys | Val | Val | Glu | |
| | | | 180 | | | | | 185 | | | | | 190 | | | |

| ata | aaa | tca | aaa | gaa | gag | gaa | agg | ctc | aac | caa | gag | aaa | aag | gtc | tct | 624 |
|---|---|---|---|---|---|---|---|---|---|---|---|---|---|---|---|---|
| Ile | Lys | Ser | Lys | Glu | Glu | Glu | Arg | Leu | Asn | Gln | Glu | Lys | Lys | Val | Ser | |
| | | 195 | | | | | 200 | | | | | 205 | | | | |

| gtt | tat | tta | gaa | gac | aca | gac | taa | | | | | | | | | 648 |
|---|---|---|---|---|---|---|---|---|---|---|---|---|---|---|---|---|
| Val | Tyr | Leu | Glu | Asp | Thr | Asp | | | | | | | | | | |
| | 210 | | | | | 215 | | | | | | | | | | |

<210> SEQ ID NO 36
<211> LENGTH: 215
<212> TYPE: PRT
<213> ORGANISM: Homo sapiens

<400> SEQUENCE: 36

Met Tyr Gly Lys Ser Ser Thr Arg Ala Val Leu Leu Leu Leu Gly Ile

```
                1               5                   10                  15
                Gln Leu Thr Ala Leu Trp Pro Ile Ala Ala Val Glu Ile Tyr Thr Ser
                            20                  25                  30

Arg Val Leu Glu Ala Val Asn Gly Thr Asp Ala Arg Leu Lys Cys Thr
                            35                  40                  45

Phe Ser Ser Phe Ala Pro Val Gly Asp Ala Leu Thr Val Thr Trp Asn
                            50                  55                  60

Phe Arg Pro Leu Asp Gly Gly Pro Glu Gln Phe Val Phe Tyr Tyr His
                65                      70                  75                  80

Ile Asp Pro Phe Gln Pro Met Ser Gly Arg Phe Lys Asp Arg Val Ser
                            85                  90                  95

Trp Asp Gly Asn Pro Glu Arg Tyr Asp Ala Ser Ile Leu Leu Trp Lys
                            100                 105                 110

Leu Gln Phe Asp Asp Asn Gly Thr Tyr Thr Cys Gln Val Lys Asn Pro
                            115                 120                 125

Pro Asp Val Asp Gly Val Ile Gly Glu Ile Arg Leu Ser Val Val His
                            130                 135                 140

Thr Val Arg Phe Ser Glu Ile His Phe Leu Ala Leu Ala Ile Gly Ser
                145                     150                 155                 160

Ala Cys Ala Leu Met Ile Ile Val Ile Val Val Leu Phe Gln
                            165                 170                 175

His Tyr Arg Lys Lys Arg Trp Ala Glu Arg Ala His Lys Val Val Glu
                            180                 185                 190

Ile Lys Ser Lys Glu Glu Glu Arg Leu Asn Gln Glu Lys Lys Val Ser
                            195                 200                 205

Val Tyr Leu Glu Asp Thr Asp
                            210                 215

<210> SEQ ID NO 37
<211> LENGTH: 648
<212> TYPE: DNA
<213> ORGANISM: Mus musculus
<220> FEATURE:
<221> NAME/KEY: CDS
<222> LOCATION: (1)..(648)
<223> OTHER INFORMATION: mEva1

<400> SEQUENCE: 37 atg tat ggc aag agc ccc gcg ctt gtg ctt cca ctt ctc ctg agt tta        48
Met Tyr Gly Lys Ser Pro Ala Leu Val Leu Pro Leu Leu Leu Ser Leu
1               5                   10                  15 cag ctc aca gcc ctt tgt cct aca gaa gct gtg gaa att tac acc tcc        96
Gln Leu Thr Ala Leu Cys Pro Thr Glu Ala Val Glu Ile Tyr Thr Ser
            20                  25                  30 ggg gcc ctg gag gca gtc aac ggg aca gat gtt cgg tta aaa tgc act       144
Gly Ala Leu Glu Ala Val Asn Gly Thr Asp Val Arg Leu Lys Cys Thr
            35                  40                  45 ttc tcc agc ttt gcc cct gtg gga gat gcg cta act gtg acg tgg aat       192
Phe Ser Ser Phe Ala Pro Val Gly Asp Ala Leu Thr Val Thr Trp Asn
            50                  55                  60 ttc cga cct cga gat ggg ggt cgt gag cag ttt gta ttc tac tac cac       240
Phe Arg Pro Arg Asp Gly Gly Arg Glu Gln Phe Val Phe Tyr Tyr His
65                      70                  75                  80 atg gac ccc ttc agg ccc atg agc gga cgg ttc aaa gac cgg gtg gtc       288
Met Asp Pro Phe Arg Pro Met Ser Gly Arg Phe Lys Asp Arg Val Val
            85                  90                  95 tgg gac gga aac ccc gag cga tat gac gtc tcc atc ttg ctc tgg aag       336
Trp Asp Gly Asn Pro Glu Arg Tyr Asp Val Ser Ile Leu Leu Trp Lys
```

```
                  100                 105                 110
ctg cag ttt gac gac aat ggg aca tac acc tgc cag gtg aag aat cca       384
Leu Gln Phe Asp Asp Asn Gly Thr Tyr Thr Cys Gln Val Lys Asn Pro
            115                 120                 125 cct gat gtt gat ggt ctg gtt ggg acg atc cgg ctc agc gtt gtg cac       432
Pro Asp Val Asp Gly Leu Val Gly Thr Ile Arg Leu Ser Val Val His
        130                 135                 140 act gtg ccc ttc tct gag atc tac ttc ctg gcc gtg gcc att ggc tct       480
Thr Val Pro Phe Ser Glu Ile Tyr Phe Leu Ala Val Ala Ile Gly Ser
145                 150                 155                 160 gcg tgc gca ctg atg atc atc gta gtg atc gtg gta gtc ctc ttc cag       528
Ala Cys Ala Leu Met Ile Ile Val Val Ile Val Val Val Leu Phe Gln
                165                 170                 175 cac ttc cgg aaa aag cga tgg gcg gac agt gct gat aaa gcc gag ggg       576
His Phe Arg Lys Lys Arg Trp Ala Asp Ser Ala Asp Lys Ala Glu Gly
            180                 185                 190 aca aaa tca aaa gaa gag gaa aaa ctc aac caa gga aac aag gtc tct       624
Thr Lys Ser Lys Glu Glu Glu Lys Leu Asn Gln Gly Asn Lys Val Ser
        195                 200                 205 gtt ttt gtg gaa gat aca gac taa                                       648
Val Phe Val Glu Asp Thr Asp
210                 215

<210> SEQ ID NO 38
<211> LENGTH: 215
<212> TYPE: PRT
<213> ORGANISM: Mus musculus

<400> SEQUENCE: 38

Met Tyr Gly Lys Ser Pro Ala Leu Val Leu Pro Leu Leu Ser Leu
1               5                   10                  15

Gln Leu Thr Ala Leu Cys Pro Thr Glu Ala Val Glu Ile Tyr Thr Ser
                20                  25                  30

Gly Ala Leu Glu Ala Val Asn Gly Thr Asp Val Arg Leu Lys Cys Thr
            35                  40                  45

Phe Ser Ser Phe Ala Pro Val Gly Asp Ala Leu Thr Val Thr Trp Asn
        50                  55                  60

Phe Arg Pro Arg Asp Gly Gly Arg Glu Gln Phe Val Phe Tyr Tyr His
65                  70                  75                  80

Met Asp Pro Phe Arg Pro Met Ser Gly Arg Phe Lys Asp Arg Val Val
                85                  90                  95

Trp Asp Gly Asn Pro Glu Arg Tyr Asp Val Ser Ile Leu Leu Trp Lys
                100                 105                 110

Leu Gln Phe Asp Asp Asn Gly Thr Tyr Thr Cys Gln Val Lys Asn Pro
            115                 120                 125

Pro Asp Val Asp Gly Leu Val Gly Thr Ile Arg Leu Ser Val Val His
        130                 135                 140

Thr Val Pro Phe Ser Glu Ile Tyr Phe Leu Ala Val Ala Ile Gly Ser
145                 150                 155                 160

Ala Cys Ala Leu Met Ile Ile Val Val Ile Val Val Val Leu Phe Gln
                165                 170                 175
```

```
His Phe Arg Lys Lys Arg Trp Ala Asp Ser Ala Asp Lys Ala Glu Gly
            180                 185                 190

Thr Lys Ser Lys Glu Glu Lys Leu Asn Gln Gly Asn Lys Val Ser
        195                 200                 205

Val Phe Val Glu Asp Thr Asp
    210                 215
```

ANTI-EVA1 PROTEIN ANTIBODY

CROSS REFERENCE TO RELATED APPLICATIONS

This application is a National Stage of International Application No. PCT/JP2016/072348, filed Jul. 29, 2016, claiming priority based on Japanese Patent Application No. 2015-152941, filed Jul. 31, 2015.

TECHNICAL FIELD

The present invention relates to an anti-Eva1 protein antibody. More specifically, the present invention relates to: an antibody comprising a complementarity-determining region (CDR) having a particular amino acid sequence, the antibody being capable of binding to a human-derived Eva1 protein; and a pharmaceutical composition such as an anticancer agent comprising the antibody as an active ingredient.

Moreover, the present application claims priority based on Japanese Patent Application No. 2015-152941 (filed on Jul. 31, 2015), the disclosures of which are incorporated by reference herein.

BACKGROUND ART

Cancers in addition to coronary artery disease are the main death cause in developed countries. The proportion of cancers is also steadily increasing year after year. Hence, the urgent development of cancer eradication therapy has been desired strongly.

In the development of cancer curative treatments, the presence of cancer stem cells has been emphasized recently. Cancer stem cells are found only in small portions of cancer tissues, but repeat self-renewal and further differentiate. Thereby, cancer stem cells are believed to be the source of generating the majority of cancer cells. In addition, while cancer stem cells have such a high tumor-forming potential, it has been suggested that cancer stem cells have high resistances to chemotherapy and radiation therapy. Hence, even if chemotherapy or radiation therapy can kill the most of cancer cells in cancer tissues, cancer stem cells survive, so that the relapse, metastasis, and the like of the cancer occur. Accordingly, if targeting cancer stem cells can lead to killing of the cells, the development of a treatment method is expected which is also useful for preventing the metastasis, relapse, and the like of the cancer.

In view of such circumstances, the present inventors have successfully identified an Eva1 protein as a protein expressed at high level in a glioma and its cancer stem cells. Further, the present inventors have revealed that the expression of this Eva1 protein correlates with the glioma malignancy, and that there is a high correlation between the survival rate of glioma patients and the expression of the Eva1 gene in the gliomas derived from the patients. Moreover, the present inventors have also found out that suppressing the function of the Eva1 gene is effective in suppressing the growth potential, tumor-forming potential, and tissue invading potential of glioma cells as well as the tumor mass-forming potential of glioma stem cells (PTL 1).

Meanwhile, the treatment against this glioma among cancers is based on a surgery with adjuvant therapy of radiation therapy and chemotherapy, but has not changed much for several decades. Particularly, no effective treatment method for the most malignant glioblastoma multiforme (GBM) of malignant gliomas of central nervous system tissues has been found. Further, although temozolomide has been used as a standard therapeutic drug against malignant gliomas, the inventors have confirmed that glioma stem cells are not susceptible to temozolomide even in an amount several times as large as its effective blood concentration. Moreover, in addition to gliomas, cancer cells exposed to such a chemotherapeutic agent acquire resistance thereto, and similarly acquire cross resistance to other multiple chemotherapeutic agents in many cases. Further, chemotherapeutic agents also cause cytotoxicity to normal cells often. To reduce such side effects, the dose or administration of chemotherapeutic agents is restricted in many cases.

Under such circumstances, recently, the use of an antibody as an anticancer agent has drawn attention, and the importance has been increasingly recognized. For example, when an antibody targeting a cancer-specific antigen is administered, the antibody is assumed to accumulate in the cancer tissue. Hence, the attack on the cancer cells can be expected through an immune system with an antibody-dependent cell-mediated cytotoxicity (ADCC) activity or a complement-dependent cytotoxicity (CDC) activity. Moreover, by binding a drug such as a cytotoxic substance or a radionuclide to an antibody in advance, the bound drug can be efficiently delivered to the tumor site. Thereby, the amount of the drug reaching to the other tissues is reduced, and consequently a reduction in side effect can be expected. If a cancer-specific antigen has an activity to induce cell death, an antibody having an agonistic activity is administered; meanwhile, if a cancer-specific antigen is involved in cell growth and survival, an antibody having a neutralizing activity is administered. In these ways, termination or shrinkage of cancer growth can be expected from the accumulation of the tumor-specific antibody and the activity of the antibody. From such abilities, it is thought that an antibody is suitably applied as an anticancer agent.

CITATION LIST

Patent Literature

[PTL 1] International Publication No. WO2012/043747

SUMMARY OF INVENTION

Technical Problem

The present invention has been made in view of such circumstances. An object of the present invention is to provide an antibody targeting an Eva1 protein expressed at high level in a cancer such as a glioma, particularly cancer stem cells, and consequently a pharmaceutical composition such as an anticancer agent comprising the antibody as an active ingredient.

Solution to Problem

The present inventors have earnestly studied to achieve the above object. As a result, the inventors have successfully obtained three types of mouse monoclonal antibodies (B2E5-48 antibody, C3 antibody, A5D11-10 antibody) which exhibit high affinities for a human-derived Eva1 protein. Moreover, regarding the B2E5-48 antibody and the C3 antibody, constant regions thereof were respectively substituted with human-derived constant regions to prepare chimeric antibodies. Then, the inventors have also found out that these mouse antibodies and chimeric antibodies have high ADCC and/or CDC activities. Further, the inventors have also revealed that administering these antibodies to mice having been subjected to melanoma cell administration suppresses the metastasis and the like of the cells to the lungs. These discoveries have led to the completion of the present invention.

More specifically, the present invention provides the following inventions.

<1> An antibody capable of binding to a human-derived Eva1 protein, the antibody having any one of the following features (a) to (c):

(a) comprising a variable region comprising, as a CDR, at least one amino acid sequence selected from the group consisting of amino acid sequences of SEQ ID NOs: 4 to 6, amino acid sequences having a homology of 80% or more with the amino acid sequences of SEQ ID NOs: 4 to 6, the amino acid sequences of SEQ ID NOs: 4 to 6 in at least any one of which one or more amino acids are substituted, deleted, added, and/or inserted, amino acid sequences of SEQ ID NOs: 10 to 12, amino acid sequences having a homology of 80% or more with the amino acid sequences of SEQ ID NOs: 10 to 12, and the amino acid sequences of SEQ ID NOs: 10 to 12 in at least any one of which one or more amino acids are substituted, deleted, added, and/or inserted;

(b) comprising a variable region comprising, as a CDR, at least one amino acid sequence selected from the group consisting of amino acid sequences of SEQ ID NOs: 16 to 18, amino acid sequences having a homology of 80% or more with the amino acid sequences of SEQ ID NOs: 16 to 18, the amino acid sequences of SEQ ID NOs: 16 to 18 in at least any one of which one or more amino acids are substituted, deleted, added, and/or inserted, amino acid sequences of SEQ ID NOs: 22 to 24, amino acid sequences having a homology of 80% or more with the amino acid sequences of SEQ ID NOs: 22 to 24, and the amino acid sequences of SEQ ID NOs: 22 to 24 in at least any one of which one or more amino acids are substituted, deleted, added, and/or inserted; and (c) comprising a variable region comprising, as a CDR, at least one amino acid sequence selected from the group consisting of amino acid sequences of SEQ ID NOs: 27 to 29, amino acid sequences having a homology of 80% or more with the amino acid sequences of SEQ ID NOs: 27 to 29, the amino acid sequences of SEQ ID NOs: 27 to 29 in at least any one of which one or more amino acids are substituted, deleted, added, and/or inserted, amino acid sequences of SEQ ID NOs: 32 to 34, amino acid sequences having a homology of 80% or more with the amino acid sequences of SEQ ID NOs: 32 to 34, and the amino acid sequences of SEQ ID NOs: 32 to 34 in at least any one of which one or more amino acids are substituted, deleted, added, and/or inserted.

<2> An antibody capable of binding to a human-derived Eva1 protein, the antibody having any one of the following features (a) to (c):

(a) comprising
a light chain variable region comprising an amino acid sequence of SEQ ID NO: 3, an amino acid sequence having a homology of 80% or more with the amino acid sequence of SEQ ID NO: 3, or the amino acid sequence of SEQ ID NO: 3 in at least any portion of which one or more amino acids are substituted, deleted, added, and/or inserted, and
a heavy chain variable region comprising an amino acid sequence of SEQ ID NO: 9, an amino acid sequence having a homology of 80% or more with the amino acid sequence of SEQ ID NO: 9, or the amino acid sequence of SEQ ID NO: 9 in at least any portion of which one or more amino acids are substituted, deleted, added, and/or inserted;

(b) comprising
a light chain variable region comprising an amino acid sequence of SEQ ID NO: 15, an amino acid sequence having a homology of 80% or more with the amino acid sequence of SEQ ID NO: 15, or the amino acid sequence of SEQ ID NO: 15 in at least any portion of which one or more amino acids are substituted, deleted, added, and/or inserted, and
a heavy chain variable region comprising an amino acid sequence of SEQ ID NO: 21, an amino acid sequence having a homology of 80% or more with the amino acid sequence of SEQ ID NO: 21, or the amino acid sequence of SEQ ID NO: 21 in at least any portion of which one or more amino acids are substituted, deleted, added, and/or inserted; and (c) comprising
a light chain variable region comprising an amino acid sequence of SEQ ID NO: 26, an amino acid sequence having a homology of 80% or more with the amino acid sequence of SEQ ID NO: 26, or the amino acid sequence of SEQ ID NO: 26 in at least any portion of which one or more amino acids are substituted, deleted, added, and/or inserted, and
a heavy chain variable region comprising an amino acid sequence of SEQ ID NO: 31, an amino acid sequence having a homology of 80% or more with the amino acid sequence of SEQ ID NO: 31, or the amino acid sequence of SEQ ID NO: 31 in at least any portion of which one or more amino acids are substituted, deleted, added, and/or inserted.

<3> The antibody according to <1> or <2>, comprising a human-derived constant region.

<4> The antibody according to any one of <1> to <3>, wherein the antibody has at least one cytotoxicity activity selected from an ADCC activity and a CDC activity.

<5> A pharmaceutical composition comprising the antibody according to any one of <1> to <4> as an active ingredient.

<6> The pharmaceutical composition according to <5>, wherein the pharmaceutical composition is an anticancer agent.

Note that: the B2E5-48 antibody has a light chain variable region whose amino acid sequence is the amino acid sequence of SEQ ID NO: 3; the B2E5-48 antibody has light chain CDRs 1 to 3 whose amino acid sequences are the amino acid sequences of SEQ ID NOs: 4 to 6; the B2E5-48 antibody has a heavy chain variable region whose amino acid sequence is the amino acid sequence of SEQ ID NO: 9; and the B2E5-48 antibody has heavy chain CDRs 1 to 3 whose amino acid sequences are the amino acid sequences of SEQ ID NOs: 10 to 12. Moreover, the C3 antibody has a light chain variable region whose amino acid sequence is the amino acid sequence of SEQ ID NO: 15; the C3 antibody has light chain CDRs 1 to 3 whose amino acid sequences are the amino acid sequences of SEQ ID NOs: 16 to 18; the C3 antibody has a heavy chain variable region whose amino acid sequence is the amino acid sequence of SEQ ID NO: 21; and the C3 antibody has heavy chain CDRs 1 to 3 whose amino acid sequences are the amino acid sequences of SEQ ID NOs: 22 to 24. Further, the A5D11-10 antibody has a light chain variable region whose amino acid sequence is the amino acid sequence of SEQ ID NO: 26; the A5D11-10 antibody has light chain CDRs 1 to 3 whose amino acid sequences are the amino acid sequences of SEQ ID NOs: 27 to 29; the A5D11-10 antibody has a heavy chain variable region whose amino acid sequence is the amino acid sequence of SEQ ID NO: 31; and the A5D11-10 antibody has heavy chain CDRs 1 to 3 whose amino acid sequences are the amino acid sequences of SEQ ID NOs: 32 to 34.

Advantageous Effects of Invention

According to the present invention, it is possible to provide an antibody which exhibits a high affinity for a human-derived Eva1 protein and has high ADCC and/or CDC activities. Further, the antibody of the present invention exhibits a high anti-tumor activity in vivo, too, thus enabling cancer treatment or prevention including cancer metastasis suppression, relapse suppression, and the like, as well.

BRIEF DESCRIPTION OF DRAWINGS

FIG. 1 is a figure showing the amino acid sequences of a heavy chain variable region (VH) and a light chain variable region (VL) of a B2E5-48 antibody, an anti-Eva1 protein antibody of the present invention. In the figure, the underlined amino acid sequences indicate CDRs 1 to 3 in each variable region. Moreover, the amino acid sequences of the light chain variable region and the heavy chain variable region of the B2E5-48 antibody are respectively amino acid sequences of SEQ ID NOs: 3 and 9.

FIG. 2 is a figure showing the amino acid sequences of a heavy chain variable region (VH) and a light chain variable region (VL) of a C3 antibody, an anti-Eva1 protein antibody of the present invention. In the figure, the underlined amino acid sequences indicate CDRs 1 to 3 in each variable region. Moreover, the amino acid sequences of the light chain variable region and the heavy chain variable region of the C3 antibody are respectively amino acid sequences of SEQ ID NOs: 15 and 21.

FIG. 3 is a figure showing the amino acid sequences of a heavy chain variable region (VH) and a light chain variable region (VL) of an A5D11-10 antibody, an anti-Eva1 protein antibody of the present invention. In the figure, the underlined amino acid sequences indicate CDRs 1 to 3 in each variable region. Moreover, the amino acid sequences of the light chain variable region and the heavy chain variable region of the A5D11-10 antibody are respectively amino acid sequences of SEQ ID NOs: 26 and 31.

DESCRIPTION OF EMBODIMENTS

<Antibody Against Human-Derived Eva1 Protein>

Figure 4:
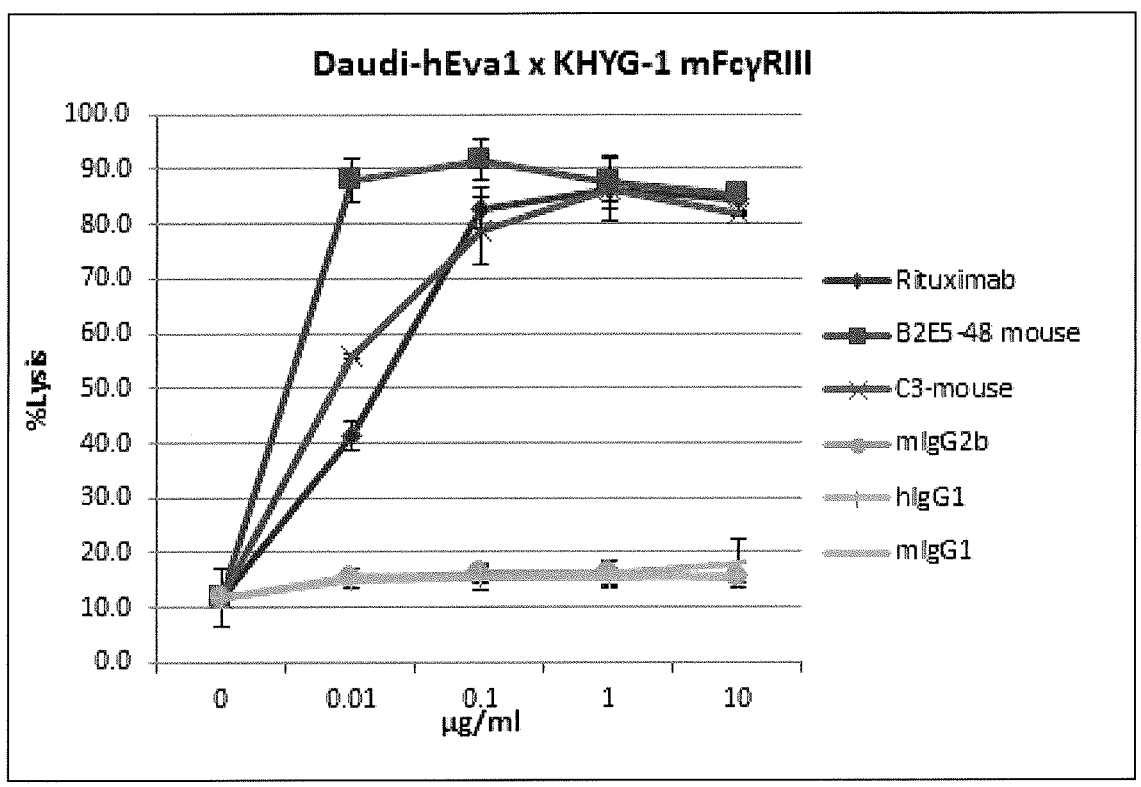
FIG. 4 is a graph showing the result of analyzing the ADCC activity of the anti-Eva1 protein mouse antibodies of the present invention against Daudi cells expressing a human Eva1 protein. In the figure, the vertical axis represents the percentage of the cells lysed, and the horizontal axis represents the concentration of the antibody added to the cells (hereinafter, regarding the representations in the figure, the same shall apply also to FIGS. 5 to 14).
Figure 5:
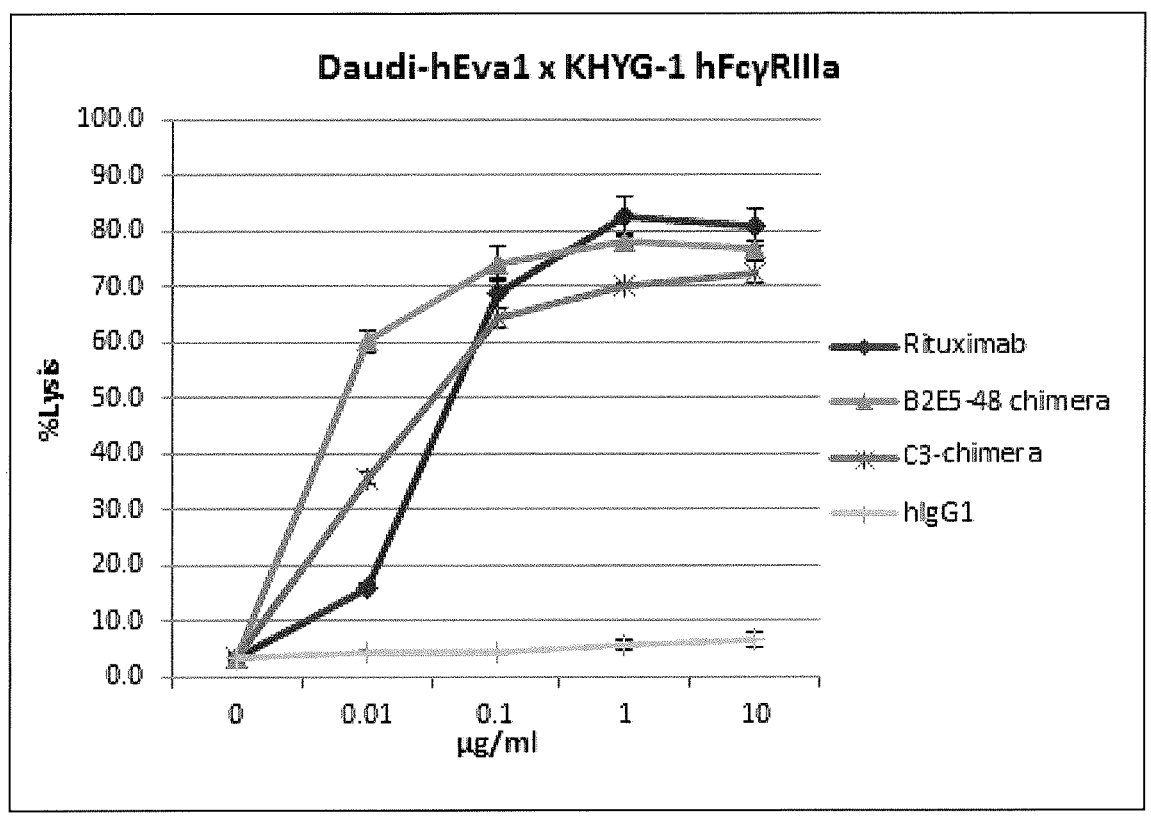
FIG. 5 is a graph showing the result of analyzing the ADCC activity of anti-Eva1 protein chimeric antibodies of the present invention against the Daudi cells expressing the human Eva1 protein.

As described in Examples later, the present inventors have successfully obtained three types of mouse monoclonal antibodies (B2E5-48 antibody, C3 antibody, A5D11-10 antibody) which exhibit high affinities for a human-derived Eva1 protein. Further, the inventors have also found out that the antibodies have high ADCC and/or CDC activities. Moreover, the inventors have also revealed that administering the antibodies to mice having been subjected to melanoma cell administration suppresses the metastasis and the like of the cells to the lungs. Furthermore, the sequences of complementarity-determining regions (CDRs) 1 to 3 in light chain variable regions and heavy chain variable regions of these antibodies have also been determined.

Based on these matters, the present invention provides an antibody capable of binding to a human-derived Eva1 protein, the antibody having a feature of comprising a variable region comprising, as a CDR, any one of the following amino acid sequences, an amino acid sequence having a homology of 80% or more, preferably 85% or more, more preferably 90% or more, and further preferably 95% or more (for example, 96% or more, 97% or more, 98% or more, 99% or more), with any one of the following amino acid sequences, or any one of the following amino acid sequences in which one or more amino acids are substituted, deleted, added, and/or inserted:

amino acid sequences of light chain CDRs 1 to 3 of the B2E5-48 antibody (amino acid sequences of SEQ ID NOs: 4 to 6), amino acid sequences of heavy chain CDRs 1 to 3 of the B2E5-48 antibody (amino acid sequences of SEQ ID NOs: 10 to 12), amino acid sequences of light chain CDRs 1 to 3 of the C3 antibody (amino acid sequences of SEQ ID NOs: 16 to 18), amino acid sequences of heavy chain CDRs 1 to 3 of the C3 antibody (amino acid sequences of SEQ ID NOs: 22 to 24), amino acid sequences of light chain CDRs 1 to 3 of the A5D11-10 antibody (amino acid sequences of SEQ ID NOs: 27 to 29), and amino acid sequences of heavy chain CDRs 1 to 3 of the A5D11-10 antibody (amino acid sequences of SEQ ID NOs: 32 to 34). Note that the term "homology" used herein includes "identity."

Moreover, a more preferable embodiment of the present invention includes the following antibody.

An antibody capable of binding to a human-derived Eva1 protein, the antibody having any one of the following features (a) to (c):

(a) comprising
  a light chain variable region comprising amino acid sequences of SEQ ID NOs: 4 to 6 as light chain CDRs 1 to 3, and
  a heavy chain variable region comprising amino acid sequences of SEQ ID NOs: 10 to 12 as heavy chain CDRs 1 to 3;

(b) comprising
  a light chain variable region comprising amino acid sequences of SEQ ID NOs: 16 to 18 as light chain CDRs 1 to 3, and
  a heavy chain variable region comprising amino acid sequences of SEQ ID NOs: 22 to 24 as heavy chain CDRs 1 to 3; and (c) comprising
  a light chain variable region comprising amino acid sequences of SEQ ID NOs: 27 to 29 as light chain CDRs 1 to 3, and
  a heavy chain variable region comprising amino acid sequences of SEQ ID NOs: 32 to 34 as heavy chain CDRs 1 to 3.

Here, all of the above CDRs may be amino acid sequences having a homology (or identity) of 80% or more, preferably 85% or more, more preferably 90% or more, and further preferably 95% or more (for example, 96% or more, 97% or more, 98% or more, 99% or more), with the amino acid sequences specified under the corresponding SEQ ID NOs, or may be the amino acid sequences specified under the corresponding SEQ ID NOs in which one or more amino acids are substituted, deleted, added, and/or inserted.

Moreover, a further preferable embodiment of the present invention includes the following antibody. An antibody capable of binding to a human-derived Eva1 protein, the antibody having any one of the following features (a) to (c):

(a) comprising
  an amino acid sequence of a light chain variable region of the B2E5-48 antibody (amino acid sequence of SEQ ID NO: 3) and
  an amino acid sequence of a heavy chain variable region of the B2E5-48 antibody (an amino acid sequence of SEQ ID NO: 9);

(b) comprising
  an amino acid sequence of a light chain variable region of the C3 antibody (an amino acid sequence of SEQ ID NO: 15) and
  an amino acid sequence of a heavy chain variable region of the C3 antibody (an amino acid sequence of SEQ ID NO: 21); and (c) comprising an amino acid sequence of a light chain variable region of the A5D11-10 antibody (an amino acid sequence of SEQ ID NO: 26) and a heavy chain variable region of the A5D11-10 antibody (an amino acid sequence of SEQ ID NO: 31).

Here, all of the above variable regions may be amino acid sequences having a homology (or identity) of 80% or more, preferably 85% or more, more preferably 90% or more, and further preferably 95% or more (for example, 96% or more, 97% or more, 98% or more, 99% or more), with the amino acid sequences specified under the corresponding SEQ ID NOs, or may be the amino acid sequences specified under the corresponding SEQ ID NOs in which one or more amino acids are substituted, deleted, added, and/or inserted.

Note that, regarding the amino acid modifications (substitution, deletion, addition, and/or insertion), see the description to be described later. Meanwhile, among these antibodies, the antibody having the feature (a) is preferable from the viewpoint that the ADCC and CDC activities to be described later are higher.

In the present invention, the term "Eva (Epithelial V-like antigen) 1 protein" refers to a single-pass transmembrane-type cell membrane protein which is a molecule also referred to as MPZL2 (Myelin protein Zero-like 2) and is involved in a cytoskeletal system. If derived from human, the protein typically has an amino acid sequence of SEQ ID NO: 36 (the protein is encoded by a nucleotide sequence of SEQ ID NO: 35). Nevertheless, the DNA sequence of a gene is mutated naturally (i.e., non-artificially) by a mutation or the like, and the amino acid sequence of a protein encoded by the gene is also modified accordingly. Thus, the "Eva1 protein" according to the present invention is not limited to the protein having the typical amino acid sequence, and also includes such naturally-occurring mutants.

In the present invention, the "antibody" includes all classes and subclasses of immunoglobulins. The "antibody" includes a polyclonal antibody and a monoclonal antibody, and also means to include the form of a functional fragment of an antibody. A "polyclonal antibody" is an antibody preparation containing different antibodies against different epitopes. Meanwhile, a "monoclonal antibody" means an antibody (including an antibody fragment) obtained from a substantially uniform antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

The antibody of the present invention has an affinity for a human Eva1 protein such that the $K_D$ (dissociation constant) value is preferably $10^{-8}$ or less, more preferably $10^{-9}$ or less. Furthermore, the $k_d$ (dissociation rate constant) value is preferably $10^{-3}$ or less. Note that a $K_D$ value and a $k_d$ value can be determined by surface plasmon resonance analysis as described later in Examples. Meanwhile, the antibody of the present invention may be an antibody capable of binding to Eva1 proteins derived from other animals (for example, a mouse Eva1 protein (typically, the protein has an amino acid sequence of SEQ ID NO: 38, the protein is encoded by a nucleotide sequence of SEQ ID NO: 37)) besides the human Eva1 protein.

The antibody capable of binding to the human Eva1 protein of the present invention desirably has at least one cytotoxicity activity selected from an ADCC activity and a CDC activity, and more desirably has an ADCC activity and a CDC activity.

In the present invention, the term "ADCC activity (antibody-dependent cell-mediated cytotoxicity activity)" means an activity to kill a target cell when an antibody binds to a cell-surface antigen on the target cell and then an effector cell (immune cell such as NK cell or monocyte) further binds to an Fc region of the antibody, so that the effector cell is activated and thereby releases a factor to kill the target cell. On the other hand, the term "CDC activity (complement-dependent cytotoxicity activity)" means an activity to lyse a target cell as a result of activating a complement system by binding of an antibody to the target cell.

In addition, the antibody of the present invention is preferably an antibody having an ADCC activity in an amount of 0.01 µg/mL against a target cell expressing the human Eva1 protein. Whether or not the antibody of the present invention has such an ADCC activity can be measured, for example, by a method described later in Examples. More concretely, in a case where Daudi cells expressing a human Eva1 protein are used as target cells to evaluate the ADCC activity in terms of the percentage of the cells lysed, when 0.01 µg/mL of the anti-Eva1 antibody of the present invention is used, the ADCC activity is the percentage of the cells lysed of preferably 30% or more, more preferably 50% or more, and further preferably 70% or more.

Moreover, the antibody of the present invention is preferably an antibody having a CDC activity in an amount of 0.30 µg/mL, more preferably 0.01 µg/mL, against a target cell expressing the human Eva1 protein. Whether or not the antibody of the present invention has such a CDC activity can be measured, for example, by a method described later in Examples. More concretely, in a case where Daudi cells expressing a human Eva1 protein are used as target cells to evaluate the CDC activity in terms of the percentage of the cells lysed, when 0.30 µg/mL of the anti-Eva1 antibody of the present invention is used, the CDC activity is the percentage of the cells lysed of preferably 20% or more, more preferably 40% or more, further preferably 60 or more, and furthermore preferably 80% or more.

Desirably, the antibody of the present invention further has an anti-cancer activity. In the present invention, the term "anti-cancer activity" means at least any one activity of an activity to suppress the growth of cancer cells, an activity to induce cancer cells to die, and an activity to suppress the metastasis of cancer cells. The anti-cancer activity can be evaluated, for example, by an analysis using a cancer bearing model (such as a mouse inoculated with B16 melanoma cells) as described later in Examples. More concretely, B16 melanoma cells are, for example, intravenously administered to mice. From the following day or several weeks thereafter, an anti-Eva1 antibody is, for example, intravenously administered every day or every few days. Then, the number of colonies of the B16 melanoma cells formed in the lungs is counted, so that the in vivo anti-cancer activity can be evaluated. As negative controls, a control antibody having the same isotype may be administered, or PBS or the like may be administered. The anti-Eva1 antibody can then be determined to have an anti-cancer activity if the number of colonies formed in the anti-Eva1-antibody administration group is smaller than that in the negative-control administration group (given that the number of colonies formed in the negative-control administration group is taken as 100%, the former is preferably 60& or less, more preferably 40% or less, further preferably 20% or less, and furthermore preferably 10% or less.

The origin, type, shape, and so forth of the antibody of the present invention are not particularly limited, as long as the antibody can bind to the above-described human Eva1 protein. Concretely, the antibody of the present invention includes an antibody derived from a non-human animal (for example, mouse antibody, rat antibody, camel antibody), a human-derived antibody, a chimeric antibody, a humanized antibody, and functional fragments of these antibodies. In a case where the antibody of the present invention is administered as a pharmaceutical drug to a human, a chimeric antibody or a humanized antibody is desirable from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. Nos. 4,816, 397, 4,816,567, 5,807,715).

As the constant region of the chimeric antibody, normally, those of human-derived antibodies are used. For example, Cγ1, Cγ2, Cγ3, Cγ4, Cμ, Cδ, Cα1, Cα2, and Cε can be used as the constant region of the heavy chain. Moreover, $C_K$ and Cλ can be used as the constant region of the light chain. The amino acid sequences of these constant regions and the base sequences encoding these amino acid sequences are known. In addition, to improve the stability of the antibody itself or the stability of the antibody production, one or amino acids in the constant regions of the human-derived antibodies may be substituted, deleted, added, and/or inserted.

In the present invention, a "humanized antibody" is an antibody obtained by grafting (CDR grafting) a gene sequence of an antigen-binding site (CDR) of a non-human (such as mouse)-derived antibody onto a human-derived antibody gene. The preparation methods such as overlap extension PCR are known (for example, European Patent Application Publication No. 239400, European Patent Application Publication No. 125023, International Publication No. WO90/07861, International Publication No. WO96/02576). A variable region of an antibody is normally composed of three CDRs flanked by four FRs. CDRs are regions substantially determining the binding specificity of an antibody. While the amino acid sequences of CDRs are rich in diversity, the amino acid sequences of FRs often show a high homology even among antibodies having different binding specificities. For this reason, generally it is said that grafting CDRs enables transfer of the binding specificity of a certain antibody to another antibody. Moreover, from the viewpoint of maintaining the function of a CDR, in grafting a non-human-derived CDR onto a human FR, a human FR having a high homology with a FR derived from the non-human animal is selected. In other words, since amino acids in a CDR not only recognize an antigen, but also coordinate with amino acids of FRs next to the CDR, and are also involved in the maintenance of the loop structure of the CDR, it is preferable to utilize a human FR whose amino acid sequence has a high homology with the amino acid sequence of a FR adjacent to the CDR to be grafted.

Known human FRs having a high homology with FRs derived from non-human animals can be searched, for example, by utilizing an antibody-dedicated search system (bioinf.org.uk/abysis/) available in the Internet. To match with the sequence of a human FR thus obtained, a mutation can be introduced into the sequence of a non-human-derived antibody other than those of CDRs. Alternatively, if a gene (cDNA) encoding the amino acid sequence of a human FR obtained by searching is available, a non-human-derived CDR may be introduced into the sequence. A mutation can be introduced, for example, by using techniques known in the art, such as nucleic acid synthesis, site-directed mutagenesis, and so forth.

The binding activity of a humanized antibody thus prepared to an antigen is qualitatively or quantitatively measured and evaluated, so that FRs of a human-derived antibody can be suitably selected which enables CDRs to forma favorable antigen-binding site when the FRs ligated to each other with the CDRs in between. Additionally, as necessary, according to a method described in Sato, K. et al., Cancer Res, 1993, 53, 851-856 or the like, amino acid residues of FRs can also be substituted so that CDRs of the humanized antibody can form an appropriate antigen-binding site. Further, the binding activity of the amino acid-substituted mutant antibody to an antigen is measured and evaluated, so that a mutated FR sequence having a desired characteristic can be selected.

In the present invention, a "functional fragment" of an antibody means a part (partial fragment) of the antibody, which specifically recognizes the human-derived Eva1 protein. Concrete examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

Here, "Fab" means a monovalent antigen-binding fragment of an immunoglobulin, composed of a part of one light chain and a part of one heavy chain. Fab can be obtained by papain digestion of an antibody or by a recombinant method. "Fab'" is different from Fab in that a small number of residues, including one or more cysteines in an antibody hinge region, are added to the carboxy terminus of a heavy chain CH1 domain. "F(ab') 2" means a bivalent antigen-binding fragment of an immunoglobulin, composed of parts of two light chains and parts of two heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (scFv)" includes a heavy chain variable region and a light chain variable region of an antibody, and these regions exist in a single polypeptide chain. A "sc (Fv) 2" is a single chain obtained by linking two heavy chain variable regions and two light chain variable regions with a linker or the like. A "diabody" is a small antibody fragment having two antigen-binding sites. This fragment includes a heavy chain variable region linked to a light chain variable region in a single polypeptide chain, and each region forms a pair with a complementary region of another chain. A "polyspecific antibody" is a monoclonal antibody having binding specificities to at least two different antigens. For example, a polyspecific antibody can be prepared by coexpression of two immunoglobulin heavy chain/light chain pairs in which the two heavy chains have different specificities.

The antibody of the present invention includes antibodies whose amino acid sequences are modified without impairing desirable activities (affinity for an antigen, ADCC activity, CDC activity, anti-cancer activity, and/or other biological properties). Such an amino acid sequence mutant can be prepared, for example, by introduction of a mutation into a DNA encoding an antibody chain of the B2E5-48 antibody, the C3 antibody, or the A5D11-10 antibody to be described later, or by peptide synthesis. Examples of such a modification include substitution, deletion, addition, and/or insertion of residues in the amino acid sequence of the antibody. A site where the amino acid sequence of the antibody is modified may be a constant region of a heavy chain ora light chain of the antibody ora variable region (FR and CDR) thereof, as long as the resulting antibody has activities equivalent to those before the modification. It is conceivable that a modification on an amino acid other than those in CDR has a relatively small influence on the binding affinity for an antigen. As of now, there are known screening methods for antibodies whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008), MAbs. March-April; 6 (2):437-45 (2014)). Additionally, now, an antibody whose affinity for an antigen has been enhanced can also be modeled by utilizing an integrated computing chemical system or the like (for example, Molecular Operating Environment manufactured by CCG ULC in Canada) (see, for example, rsi.co.jp/kagaku/cs/ccg/products/applicatio n/protein.html). Further, as described in Protein Eng Des Sel. 2010 August; 23 (8): 643-51, a case has been known where CDR1 in the heavy chain variable region and CDR3 in the light chain variable region are not involved in the affinity for an antigen. Moreover, similarly, Molecular Immunology 44: 1075-1084 (2007)) has reported that, in most antibodies, CDR2 in the light chain variable region is not involved in the affinity for an antigen. As described above, regarding the affinity of the antibody for an antigen, equivalent activities can be exhibited without requiring all of CDRs 1 to 3 in each heavy chain variable region and light chain variable region. Actually, Biochem Biophys Res Commun. 2003 Jul. 18; 307 (1): 198-205, J Mol Biol. 2004 Jul. 9; 340 (3): 525-42, and J Mol Biol. 2003 Aug. 29; 331 (5): 1109-20 have reported cases where having at least one CDR of the original antibody maintains the affinity for an antigen. Thus, the antibody of the present invention also includes an antibody comprising at least one CDR of the B2E5-48 antibody, the C3 antibody, or the A5D11-10 antibody to be described later.

Moreover, the number of amino acids modified in the antibody of the present invention is preferably 10 amino acids or less, more preferably 5 amino acids or less, and most preferably 3 amino acids or less (for example, 2 amino acids or less, 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan).

In addition, the antibody of the present invention also includes an antibody wherein the amino acid sequence after modification has an antibody chain whose amino acid sequence has a homology of 80% or more at the amino acid sequence level with the antibody chain of the B2E5-48 antibody, the C3 antibody, or the A5D11-10 antibody to be described later, as long as the antibody has activities equivalent to those before the modification. The homology should be at least 80%, preferably 85% or more, more preferably 90% or more, and further preferably 95% or more (for example, 96% or more, 97% or more, 98% or more, 99% or more). Moreover, the sequence homology can be determined by utilizing the BLASTP (amino acid level) program (Altschul et al. J. Mol. Biol., 215: 403-410, 1990). This program is based on the algorithm BLAST of Karlin and Altschul (Proc. Natl. Acad. Sci. USA, 87: 2264-2268, 1990, Proc. Natl. Acad. Sci. USA, 90: 5873-5877, 1993). When an amino acid sequence is analyzed by BLASTP, the parameters are set to, for example, score=50, word length=3. Meanwhile, when an amino acid sequence is analyzed by using the Gapped BLAST program, the analysis can be conducted as described in Altschul et al. (Nucleic Acids Res. 25: 3389-3402, 1997). When the BLAST and Gapped BLAST programs are used, the default parameters of each program are used. The specific procedures of these analysis methods are known.

Moreover, "having equivalent activities" and similar phrases mean that the affinity for an antigen, the ADCC activity, the CDC activity, or the anti-cancer activity is equivalent to (for example, 70% or more, preferably 80% or more, more preferably 90% or more of) those of a target antibody (typically, the B2E5-48 antibody, the C3 antibody, the A5D11-10 antibody).

Further, the modification on the antibody of the present invention may be a modification on post-translational process of the antibody, for example, the change in the number of sites of glycosylation or in location of the glycosylation. Thereby, for example, the ADCC activity of the antibody can be improved. Glycosylation of the antibody is typically N-linked or O-linked glycosylation. The glycosylation of the antibody greatly depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. Nos. 5,047,335, 5,510,261, 5,278,299, International Publication No. WO99/54342). Further, in the present invention, for the purpose of increasing the stability of the antibody or other purposes, an amino acid subjected to deamidation or an amino acid adjacent to the amino acid subjected to the deamidation may be substituted with a different amino acid to suppress the deamidation. Moreover, the stability of the antibody can also be increased by substituting glutamic acid with a different amino acid. The present invention also provides an antibody thus stabilized.

As described later in Examples, the antibody of the present invention can be prepared by a hybridoma method, or can be prepared by a recombinant DNA method. The hybridoma method is typically a method by Kohler and Milstein (Kohler &Milstein, Nature, 256: 495 (1975)). In this method, antibody-producing cells used in the cell fusion process are spleen cells, lymph node cells, peripheral blood leucocytes, or the like of an animal (for example, mouse, rat, hamster, rabbit, monkey, goat) immunized with an antigen (a human-derived Eva1 protein, a partial peptide thereof, a protein in which an Fc protein or the like is fused to the protein or peptide, cells expressing these, or the like). It is also possible to use antibody-producing cells which are obtained by treating, with the antigen in a medium, the above-described cells, lymphocytes, or the like having been isolated from a non-immunized animal in advance. As myeloma cells, various known cell lines can be used. The antibody-producing cells and the myeloma cells may be originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to the human-derived Eva1 protein can be obtained. The monoclonal antibody against the human-derived Eva1 protein can be obtained by culturing the hybridoma, or from the ascitic fluid of a mammal having been subjected to the hybridoma administration.

The recombinant DNA method is a method by which the antibody of the present invention is produced as a recombinant antibody as follows. A DNA encoding the antibody of the present invention is cloned from a hybridoma, B cells, or the like. The cloned DNA is incorporated into an appropriate vector, which is introduced into host cells (for example, a mammalian cell line such as HEK cells, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated separately into expression vectors to transform the host cells. Alternatively, the DNAs encoding a heavy chain and a light chain may be incorporated into a single expression vector to transform the host cells (see International Publication No. WO94/11523). The antibody of the present invention can be obtained in a substantially pure and homogeneous form by culturing the host cells, followed by separation and purification of the host cells or the culture liquid. For the separation and purification of the antibody, a normal method used for polypeptide purification can be employed. Once a transgenic animal (cattle, goat, sheep, pig, or the like) incorporating the antibody gene is prepared by using a transgenic animal preparation technique, a large amount of the monoclonal antibody derived from the antibody gene can also be obtained from milk of the transgenic animal.

The present invention can also provide: the DNA encoding the antibody of the present invention; a vector comprising the DNA; host cells comprising the DNA; and a method for producing the antibody, comprising culturing the host cells and recovering the antibody.

<Composition Comprising Anti-Eva1 Antibody, Etc.>

As described in Examples later, the antibody of the present invention exhibits a high affinity for a human-derived Eva1 protein, and also exhibits an ADCC activity and/or a CDC activity and so forth. Accordingly, the antibody of the present invention can be utilized to treat or prevent a disease associated with an Eva1 protein. Thus, the present invention also provides: a pharmaceutical composition comprising the antibody of the present invention as an active ingredient (for example, an anticancer agent comprising the antibody of the present invention as an active ingredient); and a method for treating or preventing a disease associated with an Eva1 protein (for example, cancer), the method comprising the step of administering a therapeutically and prophylactically effective amount of the antibody of the present invention to a mammal including a human.

The disease associated with an Eva1 protein targeted by the antibody of the present invention should be a disease, in the development, the progression of the symptom, the exacerbation, and so forth of which the expression of the Eva1 protein is involved. An example of the disease includes cancer.

Moreover, the cancer targeted by the antibody of the present invention is not particularly limited, as long as the cancer expresses Eva1 protein and the antibody of the present invention can exhibit an ADCC activity, a CDC activity, or an anti-cancer activity thereon. Examples of the cancer include gliomas (tumors arising from neural stem cells, neural precursor cells, and neuroglial cells, for example, glioblastoma multiforme (GBM), astrocytomas, medulloblastoma, ependymoma, oligodendroglioma, choroid plexus papilloma, particularly anaplastic astrocytoma, anaplastic oligodendroastrocytoma, anaplastic oligodendroglioma), stomach cancer, melanoma, lymphoma, and breast cancer. In addition, these cancers may be primary cancers, or may be metastatic cancers. Further, the cancer according to the present invention also includes cancer stem cells.

The pharmaceutical composition comprising the antibody of the present invention as an active ingredient can be used in the form of a composition comprising the antibody of the present invention and any ingredient, for example, a saline, an aqueous solution of glucose, a phosphate buffer, or the like. The pharmaceutical composition of the present invention may be formulated in a liquid or lyophilized form as necessary, and may also optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, a phosphate buffer, aluminum hydroxide, and the like for a liquid preparation. However, the examples are not limited thereto.

The method for administering the pharmaceutical composition differs depending on the age, weight, sex, and health state of an administration target, and the like. The administration can be carried out by any administration route: oral administration and parenteral administration (for example, intravenous administration, intraarterial administration, local administration). A preferable administration method is parenteral administration, more preferably intravenous administration. The dose of the pharmaceutical composition may vary depending on the age, weight, sex, and health state of a patient, the degree of the progression of the symptom, and ingredients of the pharmaceutical composition to be administered. Nevertheless, the dose is generally 0.1 to 1000 mg, preferably 1 to 100 mg, per kg body weight for an adult per day in the case of intravenous administration.

Note that in a case where the treatment target is a brain, the presence of the blood-brain barrier (BBB) often causes a problem. However, in a patient having glioblastoma multiforme (GBM) or the like, the BBB, which a normal brain has, is not formed in a blood vessel formed in a brain tumor where angiogenesis has occurred. Hence, the antibody can be delivered to the GBM by intravenous injection or the like.

Meanwhile, even in a case where the BBB functions, the antibody of the present invention can be administered while avoiding the BBB. An example of such avoidance includes a method in which a cannula or the like is inserted by stereotactic surgery so that the antibody can be directly administered to a glioma or the like through the cannula. Further, the example includes a method in which a drug delivery system comprising the antibody of the present invention is implanted into a brain (Gill et al., Nature Med. 9:589-595 (2003) and so on). Furthermore, the example includes transfection of a BBB-straddling neuron by using a vector comprising a gene encoding the antibody of the present invention (US Patent Application Publication No. 2003/0083299 and so on).

In addition, besides the methods for avoiding the BBB, it is also possible to utilize a method in which the antibody of the present invention is incorporated into or bound to a brain barrier-permeable substance and then administered. Examples of the brain barrier-permeable substance include a liposome coupled to an antibody binding fragment capable of binding to a receptor on vascular endothelium of BBB (US Patent Application Publication No. 20020025313 and so on), low-density lipoprotein particles (US Patent Application Publication No. 20040204354 and so on), apolipoprotein E (US Patent Application Publication No. 20040131692 and so on), transferrin (US Patent Application Publication No. 2003/0129186 and so on), and a rabies virus-derived, 29-amino-acid glycoprotein (see Kumar et al., Nature, 5 Jul. 2007, vol. 448, pp. 39 to 43).

Further, by administering the antibody of the present invention while controlling the activity of a receptor or channel, the antibody can also be delivered to a glioma or the like through the BBB. Examples of such a method include: increasing the permeability of the blood-brain barrier by using a glucocorticoid blocker (US Patent Application Publication No. 2002/0065259, US Patent Application Publication No. 2003/0162695, US Patent Application Publication No. 2005/0124533 and so on); activating a potassium channel (US Patent Application Publication No. 2005/0089473 and so on); inhibiting an ABC drug transporter (US Patent Application Publication No. 2003/0073713 and so on); and cationizing the antibody of the present invention (U.S. Pat. No. 5,004,697 and so on).

Hereinabove, the description has been given of brain diseases such as gliomas. However, the method for administering the antibody of the present invention against the diseases is not limited to these. Additionally, against other diseases also, those skilled in the art can select a known method suitable for such a disease as appropriate to treat a diseased site with the antibody of the present invention as in the case of the above-described brain diseases.

<Drug for Use in Missile Therapy>

Hereinabove, preferable embodiments of the antibody of the present invention have been described. However, the antibody of the present invention is not limited to the above-described embodiments. Since the Eva1 protein targeted by the antibody of the present invention is expressed at high level in a cancer, particularly cancer stem cells, the antibody of the present invention bound to a cytotoxic substance such as, for example, a photosensitive substance, a toxic peptide, a chemotherapeutic agent, or a radioactive chemical substance is useful in what is called a missile therapy.

The photosensitive substance bound to the antibody of the present invention for the cytotoxicity activity to function may be a substance which is activated by light irradiation, so that the substance itself changes to a form for exhibiting the cytotoxicity, or may be a substance which generates a cytotoxic substance. Examples of the photosensitive substance include chlorins, chlorin e6, porfimer sodium, talaporfin sodium, verteporfin, and precursors and derivatives thereof. Examples of the toxic peptide include ribosome inactivating proteins (RIPs) such as saporin, ricin, and Shiga toxin. The chemotherapeutic agent is not particularly limited, either. Examples thereof include temozolomide, bleomycin, cisplatin, irinotecan, dexamethasone, and taxol). Moreover, the radioactive chemical substance refers to a chemical substance including a radioactive isotope, and the radioactive isotope therein is not particularly limited. Examples thereof include $^{32}P$, $^{14}C$, $^{125}I$, $^{3}H$, $^{131}I$, $^{186}Re$, and $^{188}Re$.

Additionally, one or two or more of such cytotoxic substances may be bound to the antibody. The cytotoxic substance(s) can be bound to the antibody by selecting a known method as appropriate. For example, such low-molecular-weight compounds as the photosensitive substance and the chemotherapeutic agent can be bound to the antibody by utilizing covalent bonding or non-covalent bonding. Moreover, the toxic peptide or the like can be bound to the antibody by a genetic engineering technique. Note that these antibody modification methods have been already established.

<Diagnosis Method, Diagnostic Agent>

Moreover, the antibody of the present invention is not limited to the above-described embodiments of the treatment method, the prevention method, and the drug used in these methods. The antibody of the present invention can be utilized in a diagnosis method and as a drug used in the method.

One of concrete examples of the diagnosis method of the present invention includes a diagnosis method for a disease associated with an Eva1 protein, the method comprising the step of detecting an expression of an Eva1 protein in a sample isolated from a subject, by using the antibody of the present invention.

The sample according to the present invention is not particularly limited, as long as there is a possibility that the sample contains an Eva1 protein. Examples of the sample include tissues, cells, blood, interstitial fluid, plasma, extravascular fluid, cerebrospinal fluid, synovial fluid, pleural fluid, serum, lymph, saliva, and urine. Moreover, the sample according to the present invention includes not only such tissues or cells collected from human bodies, but also fixed specimens of the tissues or cells, culture liquids of such cells, and the like.

In the present invention, when an Eva1 protein is detected in a sample, the disease is diagnosed using the level of the detection as an indicator. Concretely, if the amount of the Eva1 protein detected in the sample is large in comparison with a negative control such as a healthy subject, this indicates that the subject has the disease or is likely to have the disease in the future.

In the present invention, the Eva1 protein can be detected by immunological methods using the antibody of the present invention. Examples of such immunological methods include immunohistochemistry, enzyme-linked immunosorbent assay (ELISA), radioimmunoassay, fluorescence immunoassay, western blot, and immunoprecipitation.

Moreover, in the diagnosis method of the present invention, cells expressing an Eva1 protein in vivo can al so be detected with the antibody of the present invention. To trace the antibody administered in vivo, the antibody which is detectably labeled can be used. For example, this method includes the steps of: administering, to a subject, the antibody of the present invention to which a labeling substance is bound; and detecting accumulation of the labeling substance. For example, using a radioisotope, a fluorescent substance, or a luminescent substance as the labeling substance, the in vivo behavior of the antibody labeled with these is traced, so that the cells can be detected in vivo. When a radioisotope is used as the labeling substance, the localization of the antibody can be imaged by tracing the radioactivity. Meanwhile, the antibody labeled with a fluorescent substance or a luminescent substance can be observed by utilizing an endoscope or a laparoscope.

To detect the cells in vivo, positron emitting nuclides can be utilized as the radioisotope for labeling the antibody. For example, the antibody can be labeled with positron emitting nuclides such as $^{64}Cu$, $^{18}F$, $^{55}Co$, $^{66}Ga$, $^{68}Ga$, $^{76}Br$, $^{89}Zr$, and $^{124}I$. For labeling of the antibody with these positron emitting nuclides, known methods (Nucl Med Biol. 1999; 26 (8): 943-50., J Nucl Med. 2013; 54 (11): 1869-75. and so on) can be utilized. Further, after the antibody labeled with a positron emitting nuclide is administered to human, the radiation emitted from the radionuclide is measured from the outside of the body with a PET (positron emission tomography device), and converted to an image by a computer tomography procedure.

As described above, since the antibody of the present invention to which the labeling substance is bound is useful in the above-described diagnosis method, the present invention also provides the antibody of the present invention to which a radioisotope, a fluorescent substance, or a luminescent substance is bound.

EXAMPLES

Hereinafter, the present invention will be described more specifically based on Examples. However, the present invention is not limited to the following Examples.

Example 1

By methods described below, prepared were mouse-derived monoclonal antibodies (B2E5-48 antibody, C3 antibody, A5D11-10 antibody to be described later) which exhibited high affinities for a human Eva1 protein. Further, the amino acid sequences of variable regions of these antibodies were determined, and the complementarity-determining regions (CDRs 1 to 3) were also identified. Moreover, regarding the B2E5-48 antibody and the C3 antibody, chimeric antibodies comprising human-derived constant regions were prepared based on these antibodies.

<Preparation of Hybridomas for Producing Anti-Eva1 Antibodies>

In order to obtain the anti-Eva1 antibodies having a high affinity, first, a protein (hereinafter also referred to as "Fc-fusion Eva1") obtained by fusing an Fc site of an immunoglobulin to an extracellular domain of the human Eva1 protein, which is a region composed of amino acids at positions 27 to 150, was expressed in HEK 293 cells to prepare the antigen.

Specifically, first, a DNA encoding the aforementioned region was inserted into a pINFUS-EmIgG2bFc vector (manufactured by InvivoGen). Thereby, a pINFUSE-hEva1-mIgG2bFc vector encoding the Fc-fusion Eva1 was prepared. Next, HEK 293 cells were transfected with this plasmid vector, and the Fc-fusion Eva1 was transiently expressed. Then, 1 L of the culture supernatant of the HEK 293 cells thus obtained was treated using an affinity column with rProtein A SEPHAROSE® (manufactured by GE health care) to adsorb the Fc-fusion Eva1. Subsequently, to remove non-specific proteins, the column was washed with a solution of 20 mM Tris-HCl (pH 7.5) and 300 mM NaCl. Thereafter, a 100 mM arginine solution (pH 4.0 to 2.0) was used to serially change the pH in the column from neutral (pH 4.0) to an acid side (pH 2.0). Thereby, the Fc-fusion Eva1 was eluted. Immediately after the elution, 1 M Tris-HCl (pH 9.0) in an amount ⅒ of the eluted volume was added to adjust the pH to nearly neutral. After that, the eluted fraction was subjected to protein electrophoresis (SDS-PAGE) to identify the eluted fraction of the Fc-fusion Eva1. The protein in the fraction was concentrated. Then, in a solution of 20 mM Tris-HCl (pH 8.0), 150 mM NaCl, and 2 mM DTT, ultrafiltration was performed using HILOAD® 16/60 SUPERDEX® 200 (manufactured by GE health care). Finally, 2.92 mg of the purified product was obtained as the antigen protein.

Next, the resulting antigen protein prepared in this manner was applied together with an adjuvant to a mouse sole for the immunization. Then, a regional lymph node was collected from the immunized mouse, and lymphocytes were isolated. Subsequently, the lymphocytes were fused to mouse myeloma cells P3U1. Thus, hybridomas were prepared. Antibodies in the culture supernatants of 1000 of the resulting hybridomas prepared in this manner were reacted with 2B4 cells forced to express the human Eva1 protein. Thereby, 61 hybridomas were first selected which produced the antibodies exhibiting the positive reaction. Thereafter, 20 hybridomas were selected which produced the antibodies exhibiting a higher affinity. Further, by the limiting dilution method, 28 clones (including four clones derived from the same parental line) were finally established.

<Selection of Anti-Eva1 Antibodies by Surface Plasmon Resonance Assay>

To select hybridomas for producing antibodies having a higher antigen affinity from the 28 hybridomas, a surface plasmon resonance assay system Biacore was used to calculate the $K_D$ value and so forth of each antibody (hereinafter also referred to as "candidate antibody"). Concretely, first, an antibody capable of capturing mouse IgG was immobilized on a dextran-coated sensor chip (CMS, manufactured by GE health care). Then, this antibody captured each candidate antibody on the sensor chip. Subsequently, the antigen, that is, the Eva1 protein was flowed. Note that, in flowing the antigen, a solution of 10 mM-Tris-HCl (pH 7.5), 150 mM-NaCl, and 3 mM-EDTA (pH 8.0) was used. Moreover, as a solution for dissociating the antigen from the candidate antibody (captured candidate-antibody resuscitation solution), a 10 mM glycine solution (pH 1.7) was used. Thus, using these solutions, the binding reaction and the dissociation reaction between each candidate antibody and the antigen were detected with Biacore, and analyzed using the attached software. Hence, the dissociation constants ($K_D$), binding rate constants ($k_a$), and dissociation rate constants ($k_d$) were calculated. As a result, among the antibodies produced from the 28 hybridomas, the top four antibodies (C3 antibody, B1E4-32 antibody, B2E5-48 antibody, A5D11-10 antibody) were selected which exhibited high affinities (small $K_D$ values) and were slow in dissociation (small $k_d$ values). Note that the result of analyzing these antibodies revealed that the C3 antibody and the B1E4-32 antibody were antibodies originated from the same source. Hence, the subsequent analyses were conducted on the C3 antibody, the B2E5-48 antibody, and the A5D11-10 antibody.

Table 1 shows the $K_D$, $k_a$, and $k_d$ of these three types of antibodies with respect to the human Eva1 protein.

TABLE 1

|  | $k_a$ (1/Ms) | $k_d$ (s) | $K_D$ (M) |
|---|---|---|---|
| A5D11-10 mouse antibody | $3.64 \times 10^5$ | $2.12 \times 10^{-3}$ | $5.83 \times 10^{-9}$ |
| C3 mouse antibody | $9.18 \times 10^5$ | $8.31 \times 10^{-3}$ | $9.10 \times 10^{-9}$ |
| B2E5-48 mouse antibody | $6.89 \times 10^5$ | $8.08 \times 10^{-3}$ | $1.17 \times 10^{-8}$ |
| B2E5-48 chimeric antibody | $4.90 \times 10^5$ | $7.47 \times 10^{-3}$ | $1.52 \times 10^{-8}$ |

Moreover, a competition experiment utilizing surface plasmon resonance was conducted on these antibodies. Concretely, an antibody capable of capturing a mouse antibody was immobilized on a dextran-coated CM5 sensor chip, and the anti-Eva1 mouse monoclonal antibodies were first flowed thereon, so that these anti-Eva1 antibodies were each captured on the sensor chip. Then, the human Eva1 protein was flowed and captured on the anti-Eva1 antibodies. Further, onto the complexes of the respective anti-Eva1 antibodies with the human Eva1 protein formed on the chip, clones of an anti-Eva1 antibody different from these anti-Eva1 antibodies were flowed to analyze the presence or absence of competition among the antibodies for the recognition site on the human Eva1 protein.

The result revealed that the C3 antibody and the A5D11-10 antibody competed with each other. This suggested that the two completely or partially had a common recognition site on the human Eva1 protein. Meanwhile, the B2E5-48 antibody did not compete with any of the C3 antibody and the A5D11-10 antibody. This revealed that the B2E5-48 antibody and these antibodies recognized completely different epitopes.

In addition, the Eva1 protein is a protein highly conserved between species of mice and human, on the sequences of which only 12 amino acids are different from each other, and the homology is high (86.99%). Accordingly, in order to analyze the species specificity of each antibody, the affinity for each of the human- and mouse-derived Eva1 proteins was evaluated by employing surface plasmon resonance. The result revealed that the C3 antibody and the A5D11-10 antibody exhibited affinities for both of the human Eva1 protein and the mouse Eva1 protein. Note that, as to the C3 antibody, the affinity for the human Eva1 protein was higher than that for the mouse Eva1 protein in terms of $K_D$ value by approximately $10^{-1}$. Meanwhile, it was revealed that the B2E5-48 antibody specifically bound only to the human Eva1 protein and did not bind at all to the mouse Eva1 protein.

Further, the result of the class check demonstrated that the B2E5-48 antibody was mouse IgG2b, and that the C3 antibody was mouse IgG1.

<Epitope Analysis of B2E5-48 Antibody>

Even though the homology between the human Eva1 and the mouse Eva1 is quite high, the B2E5-48 antibody specifically recognizes only the human Eva1 protein, and no binding to the mouse Eva1 protein was observed as described above. Thus, this result suggests a possibility that the B2E5-48 antibody recognizes some of the 12 amino acids not conserved between the human Eva1 protein and the mouse Eva1 protein.

Accordingly, regarding amino acids in the Eva1 protein which are not conserved between human and mice, and whose side chains are oriented to the surface, mutants were prepared by substituting the amino acids in the human Eva1 with ones in mice. Specifically, a total of four types of human Eva1 mutants of (A43V, S96V, Q85R), (R33G, V34A, V134L, I135V, E137T), (L68R, P72R), and (I81M) were prepared and a binding experiment utilizing surface plasmon resonance was conducted.

As a result, the binding of the B2E5-48 antibody was not observed only from the (L68R and P72R) double mutant among these mutants. Thus, it was suggested that a region including these amino acids at positions 68 and 72 was the epitope of the B2E5-48 antibody. To further narrow down the responsible amino acid, single mutants (L68R or P72R) of the respective sites were prepared, and the binding experiment utilizing surface plasmon resonance was conducted. As a result, the B2E5-48 antibody completely lost the binding ability to the P72R mutant. On the other hand, for the L68R mutant, the B2E5-48 antibody kept the same $K_D$ value as that for the wild type. Thus, it was revealed that at least proline at position 72 was a recognition amino acid included in the epitope of the B2E5-48 antibody.

<Epitope Analysis of A5D11-10 Antibody>

The crystal structure of a complex of the human Eva1 protein with Fab of the A5D11-10 antibody was determined at a resolution of 2.0 Å. Based on the structure, it was revealed that the A5D11-10 antibody recognized tyrosine at position 30, threonine at position 31, arginine at position 33, lysine at position 46, threonine at position 48, phenylalanine at position 49, serine at position 51, glutamic acid at position 102, arginine at position 103, and tyrosine at position 104 of the human Eva1 protein. Based on the result of the structural analysis, tyrosine at position 30, lysine at position 46, glutamic acid at position 102, arginine at position 103, and tyrosine at position 104 on the human Eva1 protein were considered to be important for the binding. Then, mutants were prepared by substituting each of the amino acids with alanine. The binding experiment utilizing surface plasmon resonance was conducted using these mutants. The epitope of the A5D11-10 antibody was verified, and how the amino acids recognized by the antibody were important in binding was analyzed. As a result, the A5D11-10 antibody lost the binding ability to the Y30A mutant. The result of the aforementioned structural analysis had revealed that this tyrosine at position 30 formed hydrophobic bonds with the main chains of glycine at position 103 and glycine at position 104 of the heavy chain CDR3 of the A5D11-10 antibody. In addition, the side chain portion conceivably forms a hydrogen bond with serine at position 50 of the same molecule, contributing to the structural integrity. Hence, the substitution with alanine completely cleaves the hydrophobic bonds formed at the ring structure portion of the tyrosine side chain, and the hydrogen bond contributing to the stabilization is lost, so that conceivably the A5D11-10 antibody completely lost the binding ability to the human Eva1 protein. Moreover, the $K_D$ values for the K46A mutant and the Y104A mutant were enhanced by $10^{-2}$ in comparison with the human Eva1 protein (wild type), verifying a decrease in affinity. As a result of the structural analysis, a side chain of the lysine at position 46 forms hydrogen bonds with both a side chain and the main chain of aspartic acid of the light chain CDR3, and forms an intermolecular interaction with tyrosine at position 32 of the light chain CDR1. Moreover, a side chain portion of the tyrosine at position 104 forms hydrogen bonds with both a side chain and the main chain of arginine at position of the heavy chain CDR1, and forms intermolecular interactions with aspartic acid at position 102 and glycine at position 103 of the heavy chain CDR3. Hence, the substitution with alanine presumably cleaves some of the bonds, consequently increasing the $K_D$ value by $10^{-2}$. Further, in the crystal structure, glutamic acid at position 102 and arginine at position 103 form many bonds with the antibody, and approximately 25-fold increases in the $K_D$ values for the respective alanine-substituted mutants were observed. As a result of the structural analysis, glutamic acid at position 102 forms hydrogen bonds with each side chain and the main chain of serine at position 57 of the heavy chain CDR2 of the A5D11-10 antibody, and further forms hydrogen bonds with the main chains of glycine at position 55 and glycine at position 56. On the other hand, the structural analysis revealed that arginine at position 103 was immobilized by forming a hydrogen bond with aspartic acid at position 59, a side chain other than the heavy chain CDRs of the A5D11-10 antibody, and further formed a bond by an intermolecular interaction with tryptophan at position 53, thereby forming a strong bond as a whole. Hence, why the $K_D$ value was increased approximately 25-fold but the bonds were not completely lost is presumably based on the fact that, in the mutant in which arginine at position 103 was substituted with alanine, the intermolecular force with tryptophan at position 53 of the heavy chain CDR2 was retained although the force was weak. Meanwhile, in the mutant in which glutamic acid at position 102 on the human Eva1 protein forming many hydrogen bonds was substituted with alanine, even though it was expected that all the hydrogen bonds would be lost, the $K_D$ value was increased 25-fold. This means that the contribution of this side chain to the antigen-antibody binding is small.

<Epitope Analysis of C3 Antibody>

As described above, the C3 antibody presumably completely or partially competed with the A5D11-10 antibody for the recognition site on the human Eva1 protein. Accordingly, as in the epitope analysis of the A5D11-10 antibody, the binding experiment utilizing surface plasmon resonance was conducted using alanine mutants. The result revealed that the C3 antibody recognized lysine at position 46, serine at position 96, and arginine at position 103 in the human Eva1 protein. The lysine at position 46, serine at position 96, and position 103 on the human Eva1 protein recognized by the C3 antibody are amino acids also recognized by the A5D11-10 antibody. This is consistent with the competition between these two antibodies for the binding to the human Eva1 protein. However, the Y104A mutation in the human Eva1 protein remarkably decreased the binding ability of the A5D11-10 antibody, but did not influence the binding ability of the C3 antibody. On the other hand, the S96A mutation did not influence the binding ability of the A5D11-10 antibody, but influenced the binding of the C3 antibody. These suggest that the recognition sites of these antibodies partially overlap, but the recognition mechanisms are different.

<Cloning and Sequencing of Genes Encoding Anti-Eva1 Antibodies>

From, the B2E5-48 and C3 hybridomas, RNAs were extracted according to a conventional method. Then, using these as templates, 5' RACE PCR was performed with SMART or RACE cDNA Amplification Kit (manufactured by Clontech Laboratories, Inc.) to amplify cDNAs of antibody heavy chain variable regions (VH chains) in VHDHJH regions and light chain variable regions (VL chains) in VLJL regions.

Moreover, from the A5D11-10 hybridoma, RNAs were extracted according to a conventional method. RT-PCR was performed using AccuScript pfuUltra II RT-PCR Kit (manufactured by Agilent Technologies, Inc.) to amplify the DNA encoding the antibody. In the RT-PCR, a Primer mix, which is a mixture of ten types designed based on the AA sequences distinctively observed in the starting portion of the variable region, was used as a Fw primer, while the same Rev primer as used in the above RACE was used.

Then, a sequencing analysis was conducted on the cDNAs encoding the respective antibodies thus prepared. Moreover, based on the sequences obtained in this manner, the CDRs and FRs were determined in accordance with the Kabat numbering scheme. Further, the obtained sequences were subjected to IgBLAST (ncbi.nlm.nih.gov/igblast/) of NCBI. The result revealed that the gene encoding the B2E5-48 antibody had the highest homologies with heavy chain genes IGHV1S81*02/IGHD1-2*01/IGHJ2*01 and light chain genes IGKV4-68*01/IGKJ5*01. In addition, the gene encoding the C3 antibody was revealed to have the highest homologies with heavy chain genes IGHV5-12-2*01/IGHD3-1*01 and IGHD3-2*01/IGHJ4*01 and the light chain genes IGKV6-32*01/IGKJ1*01. The gene encoding the A5D11-10 antibody was revealed to have the highest homologies with heavy chain genes IGHV2-2*02/IGHD2-9*01/IGHJ4*01 and light chain genes IGKV10-96*01/IGKJ1*01.

In the heavy chain variable region of the B2E5-48 antibody, 13 bases were substituted in comparison with the above highest-homology germ cell line genes. As a result, in the amino acid sequence, serine at position 31 was changed to asparagine; glutamine at position 39 was changed to leucine; leucine at position 45 was changed to phenylalanine; serine at position 54 was changed to threonine; arginine at position 57 was changed to glycine; asparagine at position 59 was changed to aspartic acid; serine at position 66 was changed to arginine; proline at position 86 was changed to leucine; and alanine at position 97 was changed to threonine. Moreover, in the light chain variable region, 5 bases were substituted in comparison with the highest-homology germ cell line genes. As a result, in the amino acid sequence, lysine at position 18 was changed to arginine; methionine at position 21 was changed to leucine; serine at position 30 was changed to glycine; arginine at position 40 was changed to glycine; and leucine at position 49 was changed to valine.

In the heavy chain variable region of the C3 antibody, bases were substituted in comparison with the highest-homology germ cell line genes. As a result, in the amino acid sequence, serine at position 52 was changed to threonine; asparagine at position 53 was changed to threonine; glycine at position 55 was changed to alanine; and serine at position 57 was changed to arginine.

In the heavy chain variable region of the A5D11-10 antibody, 2 bases were substituted in comparison with the highest-homology germ line genes. As a result, in the amino acid sequence, glutamic acid at position 5 was substituted with glutamine; and arginine at position 30 was substituted with serine. Moreover, in the light chain variable region, bases were substituted in comparison with the highest-homology germ line genes. As a result, in the amino acid sequence, arginine at position 68 was substituted with glycine; and isoleucine at position 69 was substituted with threonine.

The identified amino acid sequences of the variable regions and CDRs of the B2E5-48 antibody, the C3 antibody, and the A5D11-10 antibody, and so forth thus obtained are shown in Sequence Listing with SEQ ID NOs shown below. In addition, FIGS. 1 to 3 also show the amino acid sequences of the variable regions and CDRs of these antibodies. Note that since the sequence of the A5D11-10 was not determined by the 5' RACE PCR analysis unlike the other two clones as described above, the signal sequences are not identified.

The base sequence encoding the signal peptide and the L chain (light chain) variable region of the B2E5-48 antibody: SEQ ID NO: 1
The amino acid sequence of the signal peptide and the L chain variable region of the B2E5-48 antibody: SEQ ID NO: 2
The amino acid sequence of the L chain variable region of the B2E5-48 antibody: SEQ ID NO: 3
The amino acid sequences of the L chain CDRs 1 to 3 of the B2E5-48 antibody: SEQ ID NOs: 4 to 6
The base sequence encoding the signal peptide and the H chain (heavy chain) variable region of the B2E5-48 antibody: SEQ ID NO: 7
The amino acid sequence of the signal peptide and the H chain variable region of the B2E5-48 antibody: SEQ ID NO: 8
The amino acid sequence of the H chain variable region of the B2E5-48 antibody: SEQ ID NO: 9
The amino acid sequences of the H chain CDRs 1 to 3 of the B2E5-48 antibody: SEQ ID NOs: 10 to 12
The base sequence encoding the signal peptide and the L chain (light chain) variable region of the C3 antibody: SEQ ID NO: 13
The amino acid sequence of the signal peptide and the L chain variable region of the C3 antibody: SEQ ID NO: 14
The amino acid sequence of the L chain variable region of the C3 antibody: SEQ ID NO: 15
The amino acid sequences of the L chain CDRs 1 to 3 of the C3 antibody: SEQ ID NOs: 16 to 18
The base sequence encoding the signal peptide and the H chain (heavy chain) variable region of the C3 antibody: SEQ ID NO: 19
The amino acid sequence of the signal peptide and the H chain variable region of the C3 antibody: SEQ ID NO: 20
The amino acid sequence of the H chain variable region of the C3 antibody: SEQ ID NO: 21
The amino acid sequences of the H chain CDRs 1 to 3 of the C3 antibody: SEQ ID NOs: 22 to 24
The base sequence encoding the L chain variable region of the A5D11-10 antibody: SEQ ID NO: 25
The amino acid sequence of the L chain variable region of the A5D11-10 antibody: SEQ ID NO: 26
The amino acid sequences of the L chain CDRs 1 to 3 of the A5D11-10 antibody: SEQ ID NOs: 27 to 29
The base sequence encoding the H chain variable region of the A5D11-10 antibody: SEQ ID NO: 30
The amino acid sequence of the H chain variable region of the A5D11-10 antibody: SEQ ID NO: 31
The amino acid sequences of the H chain CDRs 1 to 3 of the A5D11-10 antibody: SEQ ID NOs: 32 to 34.

<Purification of Antibodies>

The hybridomas for producing the C3 antibody, the B2E5-48 antibody, and the A5D11-10 antibody were respectively transplanted into nude mice, and the ascitic fluids were collected from the mice. Then, the ascitic fluids were treated with 4 M ammonium sulfate. The resulting precipitates were dialyzed and solubilized. Then, these antibodies (hereinafter also referred to as C3 mouse antibody, B2E5-48 mouse antibody, and A5D11-10 mouse antibody to be distinguished from the following chimeric antibodies) were purified with Protein G columns.

<Preparation of Chimeric Antibodies>

Chimeric antibodies in which the constant regions of the mouse-derived C3 antibody and B2E5-48 antibody were each substituted with that of a human-derived antibody were prepared as follows.

A cDNA of a heavy chain constant region of a human IgG1 antibody and a cDNA of a light chain constant region of a human IgC$_K$ antibody were respectively incorporated into pcDNA3.4 vectors (manufactured by Life Technologies Corporation). Then, the cDNA encoding the heavy chain variable region of the B2E5-48 antibody or the C3 antibody amplified by PCR was inserted into the former vector. The cDNA encoding the light chain variable region of the B2E5-48 antibody or the C3 antibody amplified by PCR was inserted into the latter vector. Subsequently, the two types of vectors thus prepared were co-introduced into EXPI293F™ cells (manufactured by Life Technologies Corporation), and subjected to agitation culturing in an EXPI293™ expression medium (manufactured by Life Technologies Corporation) under conditions of 37° C. and 8% CO2 for 7 days. Thereafter, from these culture supernatants, chimeric antibodies (hereinafter also referred to as C3 chimeric antibody and B2E5-48 chimeric antibody) were recovered and purified. For the purification, Protein G columns were used for the serial elution under an acidic condition (100 mM arginine solution, pH 4.0-2.0). Immediately thereafter, the eluates were neutralized with a ⅒ volume of 1 M Tris-HCl (pH 9.0). After that, the resultant was dialyzed with a 1 L solution of 20 mM Tris-HCl (pH 8.0) and 150 mM NaCl, and concentrated.

Further, the binding reaction and the dissociation reaction between the B2E5-48 chimeric antibody and the antigen were detected with Biacore as in the case of the mouse antibodies. Hence, the dissociation constant ($K_D$), binding rate constant ($k_a$), and dissociation rate constant ($k_d$) were calculated. Table 1 above shows the obtained result.

Example 2

The mouse antibodies and chimeric antibodies prepared as described above, which exhibited high affinities for the human Eva1 protein, were analyzed for ADCC activity, CDC activity, and in vivo anti-tumor activity by methods described below.

<ADCC Activity Analysis>

The C3 mouse antibody, the B2E5-48 mouse antibody, the C3 chimeric antibody, and the B2E5-48 chimeric antibody prepared as described above were analyzed for ADCC activity (antibody-dependent cell-mediated cytotoxicity activity). Specifically, an analysis was conducted by the following method on whether when effector cells bound to an Fc site of each of these antibodies via an Fc-γ receptor, the cells were activated to lyse target cells recognized by the antibody.

First, as the target cells, prepared were MKN28 cells (human stomach cancer cells) and Daudi cells (human Burkitt lymphoma cells) forced to express the human Eva1 protein. Note that the MKN28 cells express an Eva1 protein, but the Daudi cells originally do not. Moreover, although unillustrated, it had been confirmed by flow cytometry that all of the C3 mouse antibody, the B2E5-48 mouse antibody, the C3 chimeric antibody, the B2E5-48 chimeric antibody, and the A5D11-10 mouse antibody were capable of binding to both of the Daudi cells forced to express the human Eva1 protein (hereinafter also referred to as "Daudi-hEva1 cells") and the MKN28 cells. Further, the Daudi cells express CD20 targeted by rituximab, which will be described below, but the MKN28 cells do not.

Moreover, to each type of these target cells, before contact with each anti-Eva1 antibody as described later, calcein-AM was added in an amount of 10 μL (1 mg/ml) per 1×10$^6$ cells/mL, followed by incubation at 37° C. for 1 hour. Note that calcein-AM hardly emits fluorescence but has a cell membrane permeability, and turns into calcein through the hydrolysis by an esterase in a cell. Calcein is a membrane impermeable compound and emits a strong yellow green fluorescence. When cells are killed by an ADCC activity, calcein released from the inside of the cells emits fluorescence. In addition, as the effector cells, KHYG-1 cells (tumor cells from NK cells) in which mouse-derived Fc-γ receptor III gene was introduced and KHYG-1 cells in which human-derived Fc-γ receptor IIIa gene was introduced were prepared.

Then, to each well of a 96-well plate, one of the antibodies (concentrations thereof added: 0.01, 0.1, 1, or 10 μg/ml) and one type of the target cells (1×104) incorporating the calcein-AM were added in a total amount of 100 μL, and left standing under conditions of 37° C. and 5% CO2 for 30 minutes. Moreover, negative control groups were prepared in wells in each of which an isotype control antibody (mouse IgG2b antibody, human IgG1 antibody, and mouse IgG1 antibody) was added instead of the antibodies, and wells in which no antibody was added. Further, rituximab, which is an anti-human CD20 human-mouse chimeric antibody, has been revealed to have ADCC and CDC activities Hence, a positive control group was prepared by adding this antibody to wells. Subsequently, after incubation under conditions of 37° C. and 5% CO2, 50 μL (1×105: ten times as large as the number of the target cells added) of the effector cells were added to each well. Finally, 200 μL of each culture liquid was prepared, and cultured under conditions of 37° C. and 5% CO2 for 3 hours. Thereafter, the fluorescence value of calcein released from the inside of the cells killed by the ADCC activity, the fluorescence value of calcein autonomously released from the inside of the cells, and the fluorescence value of calcein released from the inside of the cells killed by TRITON™ X-100 (final concentration of 1%) were detected with a multilabel reader ALVO X3.

Next, based on the obtained fluorescence values, lysis percentages were calculated as follows.

Lysis percentage (%)=(the fluorescence value of calcein released from the inside of the cells killed by the ADCC activity−the fluorescence value of calcein autonomously released from the inside of the cells/the fluorescence value of calcein released from the inside of the cells killed by Triton X (final concentration of 1%)−the fluorescence value of calcein autonomously released from the inside of the cells)×100. FIGS. 4 to 7 show the obtained result.

As apparent from the result shown in FIG. 4, the B2E5-48 mouse antibody and the C3 mouse antibody both exhibited high ADCC activities against the Daudi-hEva1 cells. Moreover, the ADCC activity of the C3 mouse antibody was almost the same as that of rituximab, but the B2E5-48 mouse antibody exhibited a higher ADCC activity than these. Further, as apparent from the result shown in FIG. 5, the chimeric antibodies kept the high ADCC activities against the Daudi-hEva1 cells.

Figure 6:
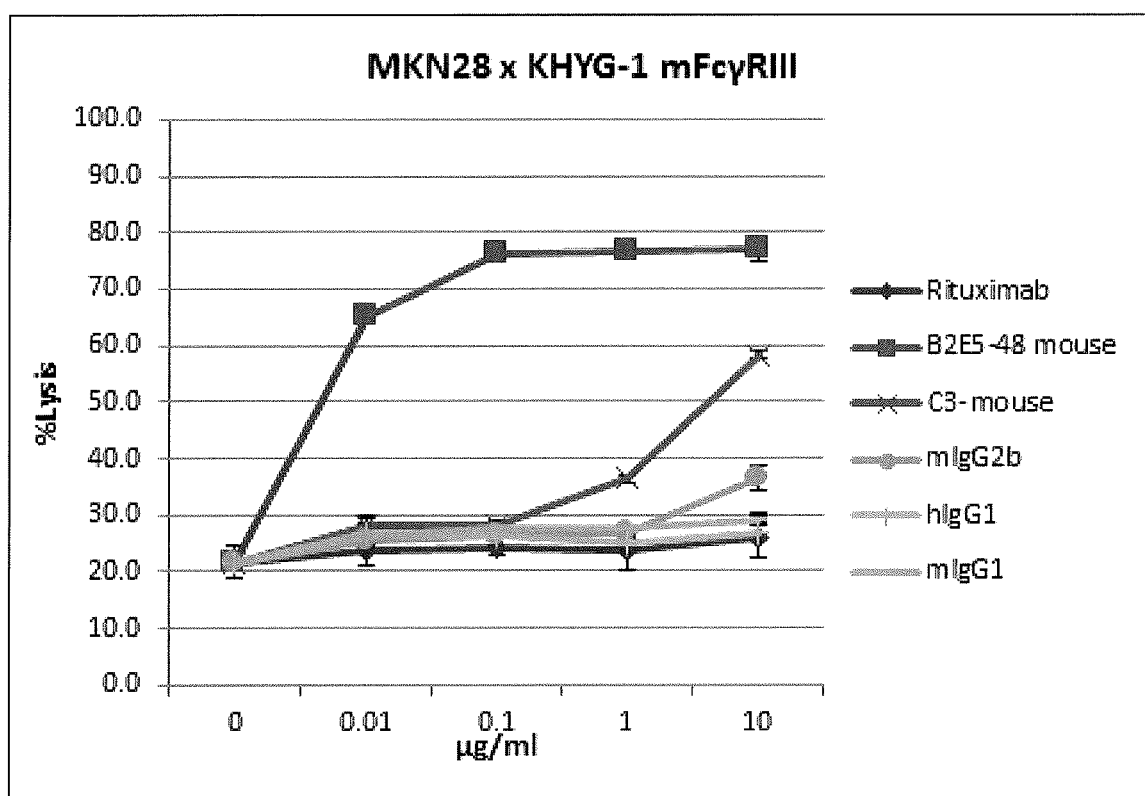
FIG. 6 is a graph showing the result of analyzing the ADCC activity of the anti-Eva1 protein mouse antibodies of the present invention against MKN28 cells.
Figure 7:
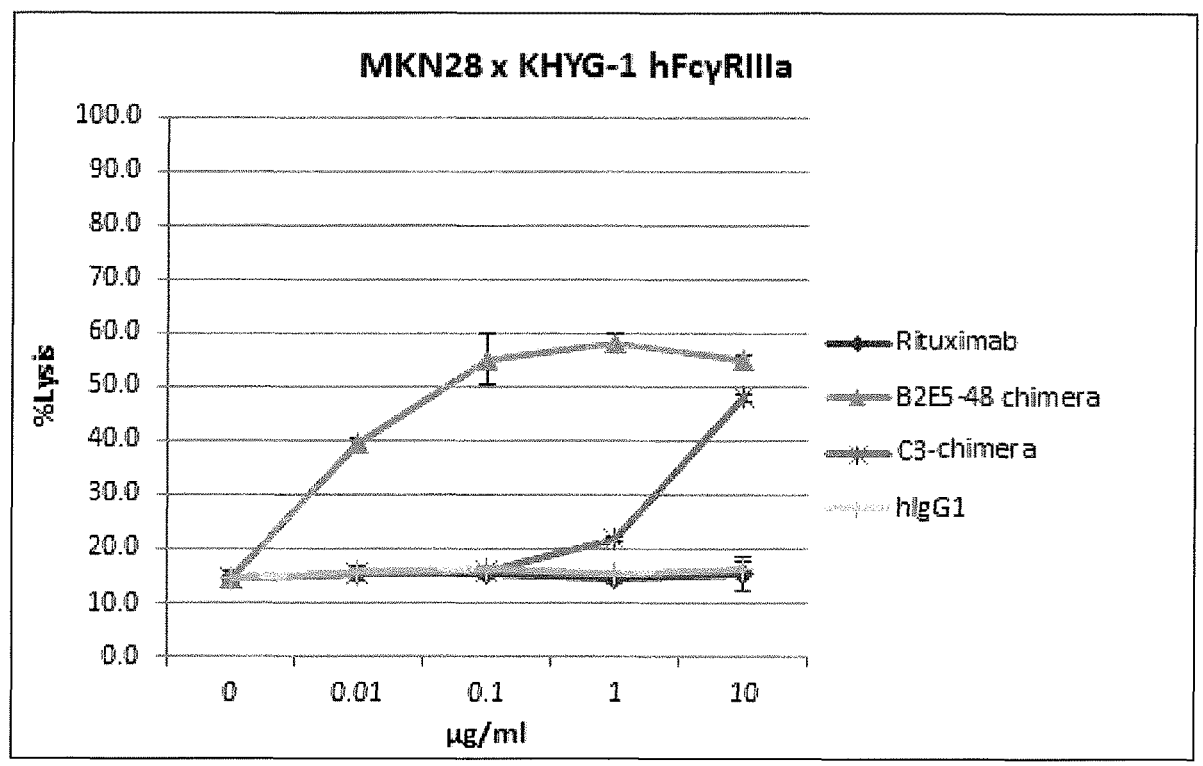
FIG. 7 is a graph showing the result of analyzing the ADCC activity of the anti-Eva1 protein chimeric antibodies of the present invention against the MKN28 cells.

In addition, as apparent from the results shown in FIGS. 6 and 7, the B2E5-48 mouse antibody, the B2E5-48 chimeric antibody, the C3 mouse antibody, and the C3 chimeric antibody all exhibited ADCC activities against the MKN28 cells, too. Particularly, the B2E5-48 mouse antibody and the B2E5-48 chimeric antibody exhibited high ADCC activities against the MKN28 cells, too.

Figure 8:
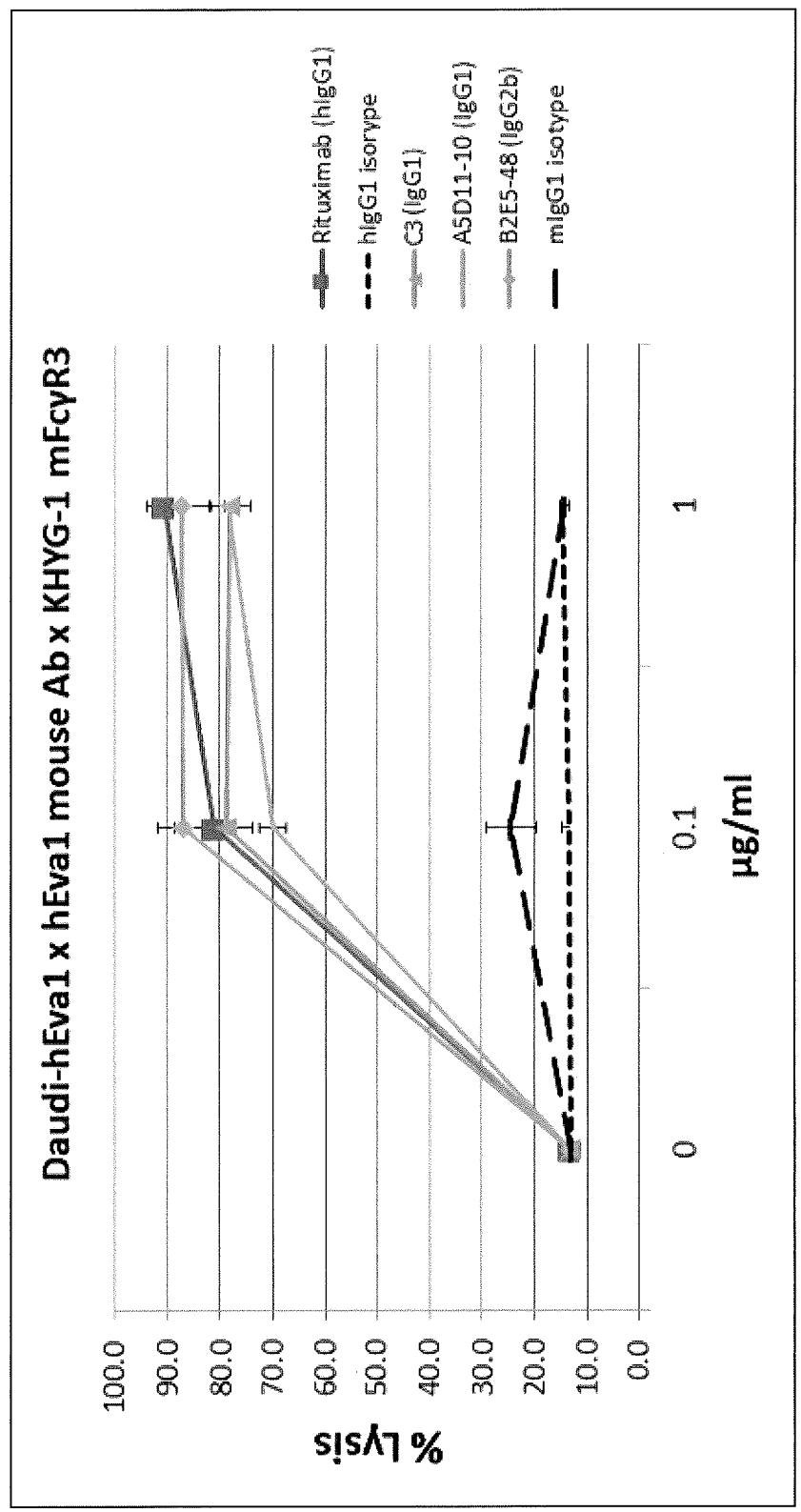
FIG. 8 is a graph showing the result of analyzing the ADCC activity of the anti-Eva1 protein mouse antibodies of the present invention against the Daudi cells expressing the human Eva1 protein.

Furthermore, the B2E5-48 mouse antibody, the C3 mouse antibody, and the A5D11-10 mouse antibody were analyzed for ADCC activity as described above by using the Daudi-hEva1 cells as the target cells, and the KHYG-1 cells as the effector cells in which the mouse-derived Fc-γ receptor III gene was introduced. FIG. 8 shows the obtained result.

As shown in FIG. 8, it was revealed that, like the B2E5-48 mouse antibody and the C3 mouse antibody, the A5D11-10 mouse antibody also exhibited a high ADCC activity against the Daudi-hEva1 cells.

<CDC Activity Analysis>

The C3 mouse antibody, the B2E5-48 mouse antibody, the C3 chimeric antibody, and the B2E5-48 chimeric antibody prepared as described above were analyzed for an activity to lyse target cells recognized by the antibody in the presence of a complement (CDC activity: complement-dependent cytotoxicity activity) by the following method.

As the target cells, the two types of cells as in the ADCC activity analysis were used. Calcein-AM was added to each cell type in an amount of 10 μL (1 mg/ml) per 1×10$^6$ cells/mL, followed by incubation at 37° C. for 1 hour. Moreover, as the complement, prepared was Low-Tox(registered trademark)-M rabbit complement (manufactured by Cedarlane Laboratories Limited, product code: CL3051).

Then, to each well of a 96U-well plate, one of the antibodies (concentrations thereof added: 0.01, 0.03, 0.1, 0.3, 1, 3, or 10 μg/ml) and one type of the target cells (1×10$^4$) were added in a total amount of 100 μL, and cultured under conditions of 37° C. and 5% CO$_2$ for 30 minutes. Moreover, negative control groups were prepared in wells in each of which an isotype control antibody (mouse IgG2b antibody and human IgG1 antibody) was added instead of the antibodies, and wells in which no antibody was added. Further, a positive control group was prepared by adding rituximab to wells. Subsequently, into each well on ice, the complement was added in an amount of 50 μL (dilution ratio: 1/64), and immediately incubated under conditions of 37° C. and 5% CO$_2$ for 2 hours. Thereafter, the plate was centrifuged under conditions of 2000 rpm and 5 minutes, and 100 μL of the supernatant was collected from each well, added to each well of a 96 flat well plate, and left standing. After that, the fluorescences, that is, the fluorescence value of calcein released from the inside of the cells killed by the complement activity, the fluorescence value of calcein autonomously released from the inside of the cells, and the fluorescence value of calcein released from the inside of the cells killed by Triton X-100 (final concentration of 1%) were detected with a multilabel reader ALVO X3 (PerkinElmer, Inc.) under conditions of ex. 485 nm and em. 535 nm. Next, based on the obtained fluorescence values, lysis percentages were calculated as follows. Lysis percentage (%)=(the fluorescence value of calcein released from the inside of the cells killed by the complement activity−the fluorescence value of calcein autonomously released from the inside of the cells/the fluorescence value of calcein released from the inside of the cells killed by Triton X (final concentration of 1%)−the fluorescence value of calcein autonomously released from the inside of the cells)×100. FIGS. 9 to 14 show the obtained result.

Figure 9:
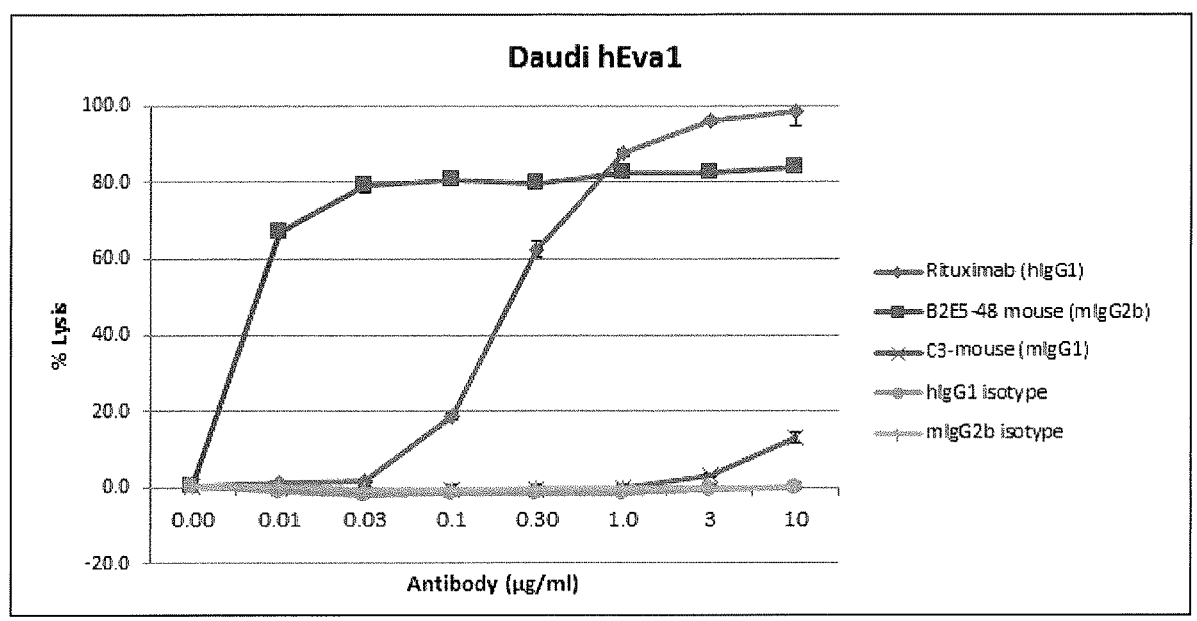
FIG. 9 is a graph showing the result of analyzing the CDC activity of the anti-Eva1 protein mouse antibodies of the present invention against the Daudi cells expressing the human Eva1 protein.

As apparent from the result shown in FIG. 9, the B2E5-48 mouse antibody exhibited a high CDC activity against the Daudi-hEva1 cells. Particularly, the activity intensity on the low concentration side was remarkably higher than that of rituximab. On the other hand, regarding the C3 mouse antibody, no CDC activity against the Daudi-hEva1 cells was observed.

Figure 10:
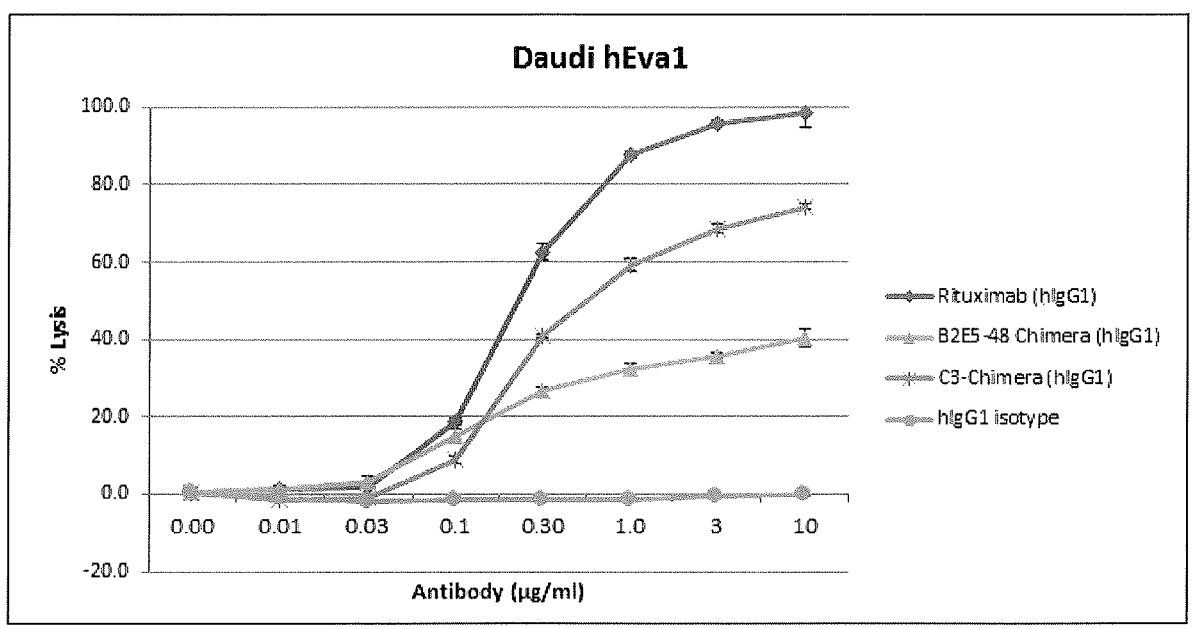
FIG. 10 is a graph showing the result of analyzing the CDC activity of the anti-Eva1 protein chimeric antibodies of the present invention against the Daudi cells expressing the human Eva1 protein.
Figure 11:
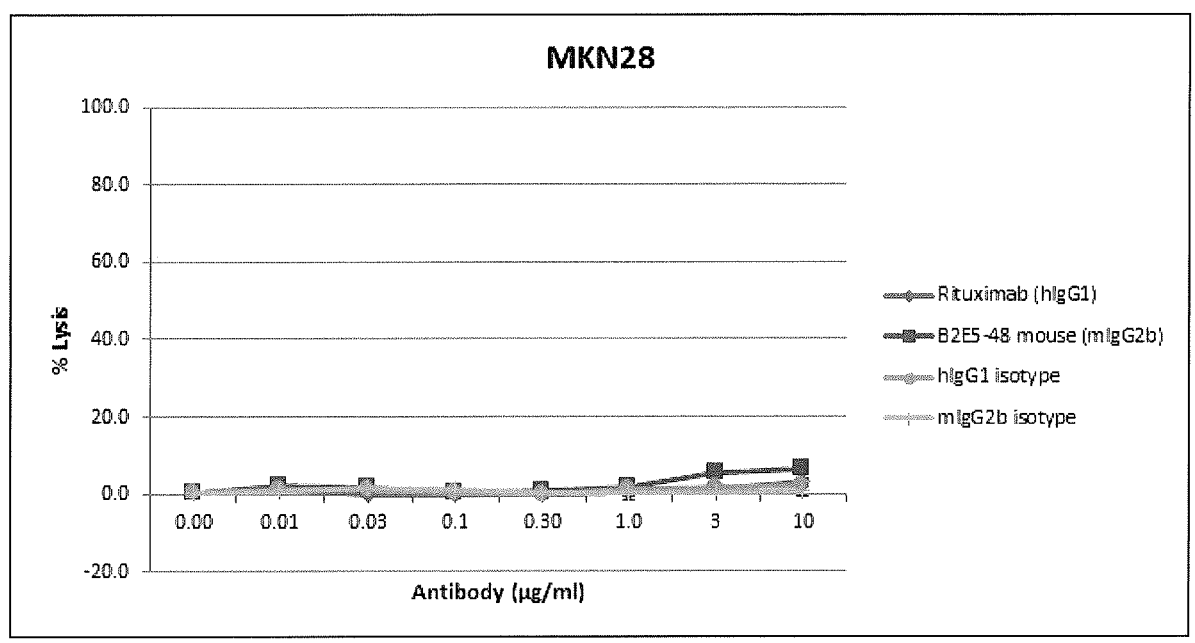
FIG. 11 is a graph showing the result of analyzing the CDC activity of the anti-Eva1 protein mouse antibody (B2E5-48 mouse antibody) of the present invention against the MKN28 cells.
Figure 12:
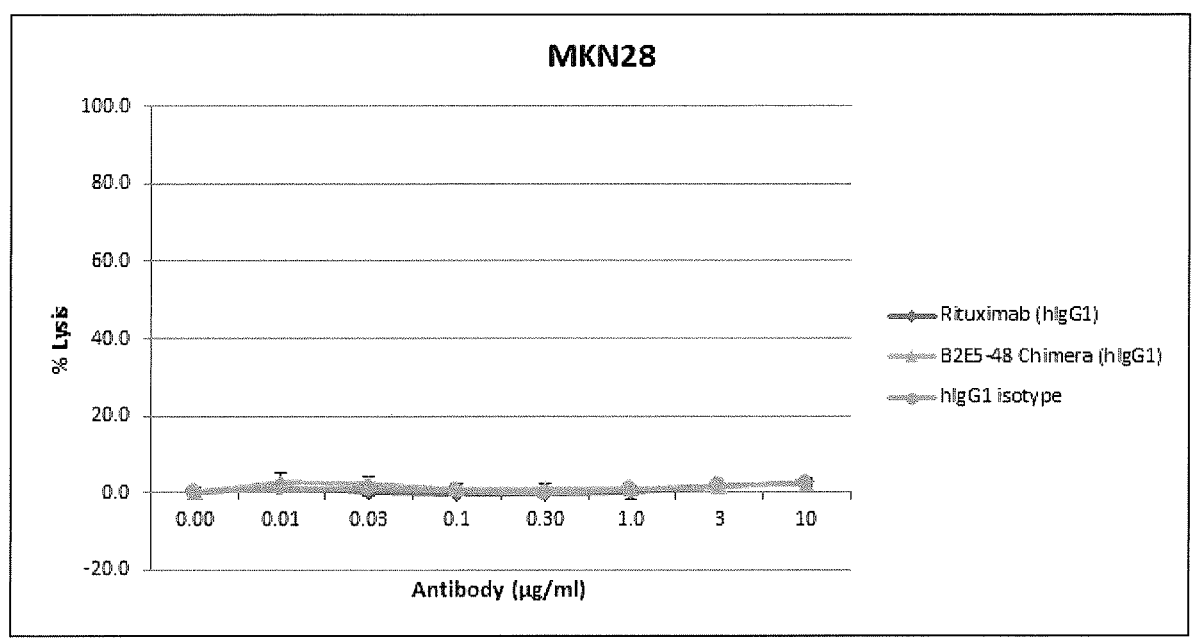
FIG. 12 is a graph showing the result of analyzing the CDC activity of the anti-Eva1 protein chimeric antibody (B2E5-48 chimeric antibody) of the present invention against the MKN28 cells.
Figure 13:
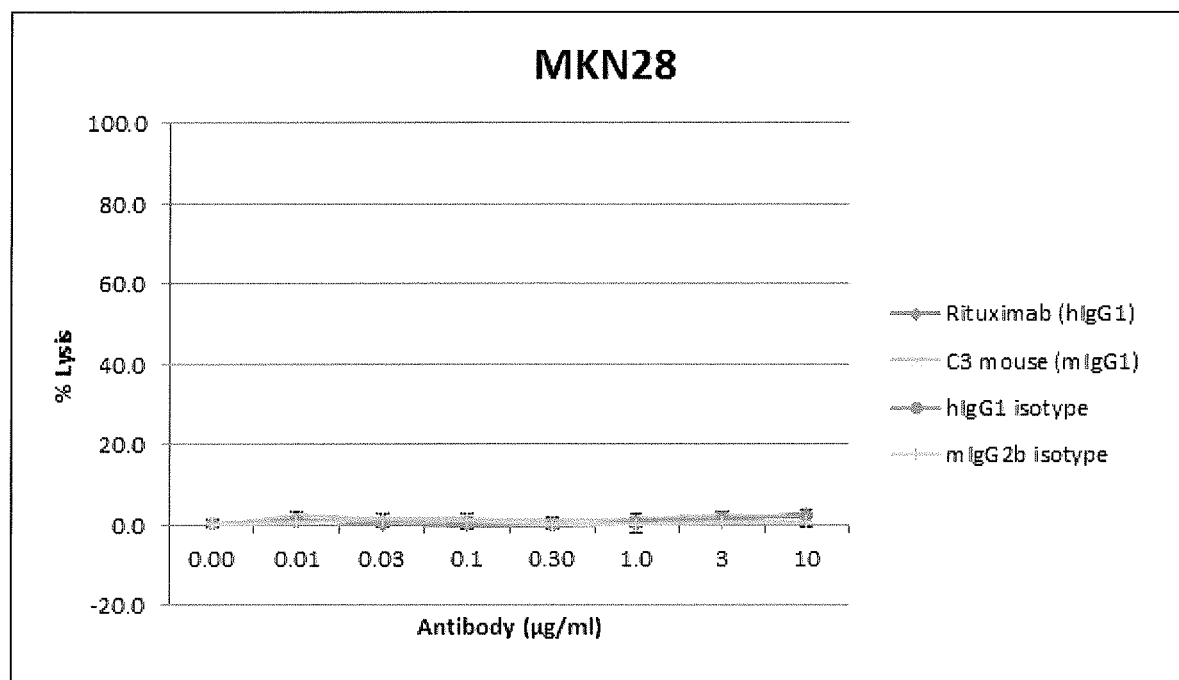
FIG. 13 is a graph showing the result of analyzing the CDC activity of the anti-Eva1 protein mouse antibody (C3 mouse antibody) of the present invention against the MKN28 cells.
Figure 14:
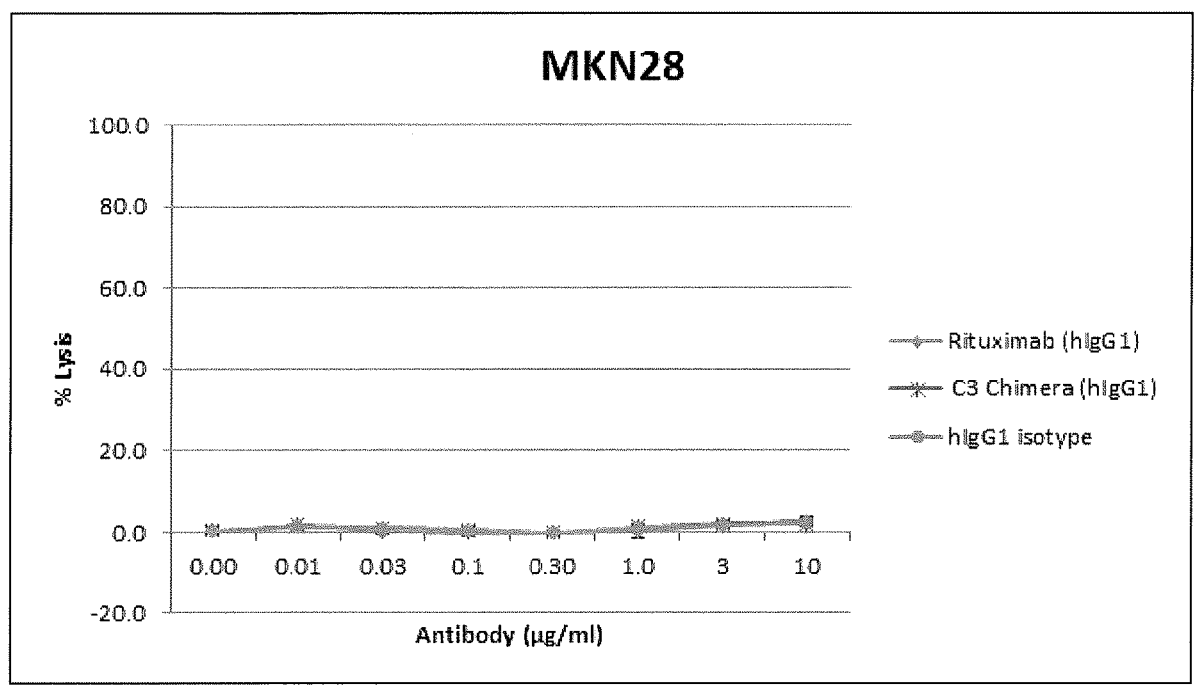
FIG. 14 is a graph showing the result of analyzing the CDC activity of the anti-Eva1 protein chimeric antibody (C3 chimeric antibody) of the present invention against the MKN28 cells.

However, as shown in FIG. 10, the chimerization made the C3 antibody have a CDC activity. Meanwhile, regarding the B2E5-48 antibody, the chimeric antibody also kept the CDC activity against the Daudi-hEva1 cells.

On the other hand, as apparent from the results shown in FIGS. 11 to 14, no CDC activity against the MKN28 cells was observed from all of the C3 mouse antibody, the B2E5-48 mouse antibody, the C3 chimeric antibody, and the B2E5-48 chimeric antibody.

Note that the difference in the CDC activities of the B2E5-48 mouse antibody against the Daudi-hEva1 cells and the MKN28 cells conceivably depended on the resistance to the CDC activity. As to the resistance to the CDC activity, there have been reports that a failure in the complement activity is induced when the distance from an antibody-binding region of a target molecule to the cell membrane is remote (J. Immunol. 174, 5706-5712, 2005), or when the complement-activity suppressing cell receptors such as CD46, CD55, and CD59 are expressed (FEBS 587, 645-651, 2013; FEES 586, 776-771, 2012; Trends in Immunology, 25, 496-503, 2004). From these reports, a possibility is speculated that the CDC activity failure not observed from the MKN28 cells but observed in the Daudi-hEva1 cells was caused by the expression of the complement-activity suppressing cell receptor on the MKN28 cells.

<Analysis with Cancer Metastasis Model Mice>

To evaluate the in vivo anti-tumor activities of the anti-Eva1 antibodies prepared as described above, the antibodies were administered to cancer metastasis model mice and analyzed as follows.

First, cells with which mice were to be inoculated for metastasis were prepared. Specifically, B16 melanoma cells (mouse B16/BL6 melanoma, received from RIKEN RBC) were maintained in an RPMI1640 medium supplemented with 10% FCS, 2 mM GlutaMAX, 100 U/mL of penicillin, and 100 μg/mL of streptomycin (all manufactured by Nacalai Tesque, Inc.) under conditions of 37° C. and 5% $CO_2$.

Note that B16 melanoma cells do not express the Eva1 protein under the culturing conditions. Inconsideration of this nature and to force the B16 melanoma cells to express the Eva1 protein, the DNA encoding the human Eva1 protein was inserted into pCMS-EGFP (manufactured by Clontech Laboratories, Inc.) to prepare a pCMS-EGFP-human Eva1 vector. Then, the pCMS-EGFP-human Eva1 or pCMS-EGFP was introduced into the B16 melanoma cells by using an AMAXA Nucleofector system (manufactured by Lonza Group). Subsequently, targeting these transformed cells, flow cytometry (the flow cytometer used: FACS Aria II, manufactured by BD Biosciences) was repeated, and GFP-positive cells were purified. Hereinafter, the resulting purified cells in which the pCMS-EGFP-human Eva1 was introduced will also be referred to as "B16-Eva1", and the resulting purified cells in which the pCMS-EGFP was introduced will also be referred to as "B16-GFP".

Next, under the following conditions (1) to (4), the GFP-positive B16 melanoma cells were inoculated into mice, and further the anti-Eva1 antibodies prepared as described above were administered thereto to evaluate the in vivo anti-tumor activities of these antibodies.

Figure 15:
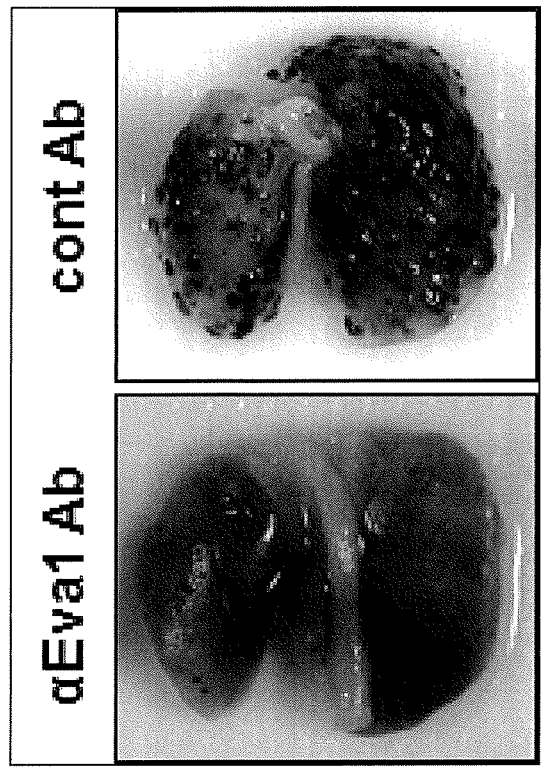
FIG. 15 shows photographs for illustrating the result of observing melanoma colonies formed in lungs of mice to which B16 melanoma cells expressing the human Eva1 protein were administered, and from day 1 thereafter the B2E5-48 mouse antibody was administered. In the figure, the result of administering the B2E5-48 mouse antibody is shown at the bottom, and the result of administering not the antibody but an isotype control antibody thereof is shown at the top.
Figure 16:
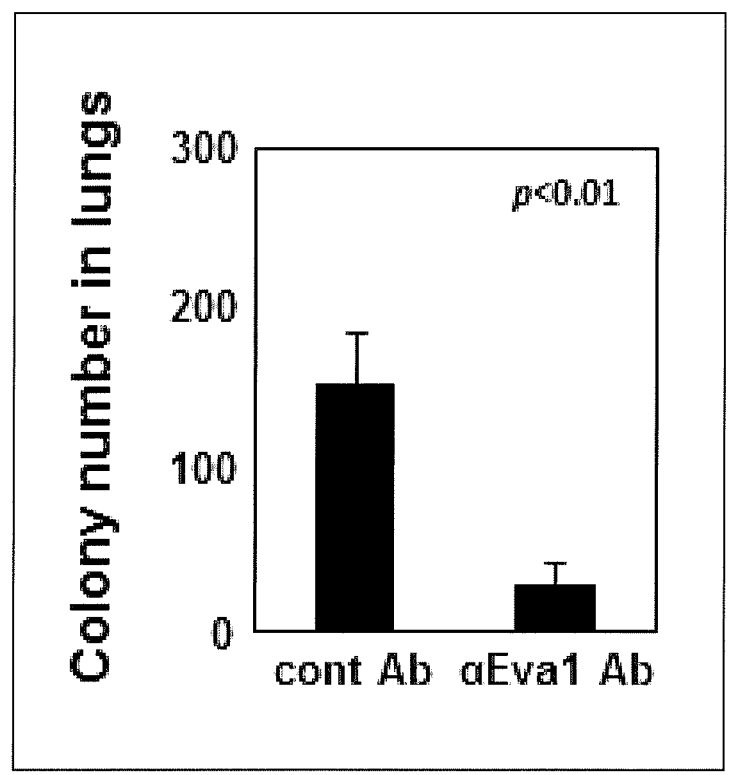
FIG. 16 is a graph showing the result of counting the number of melanoma colonies formed in the lungs of the mice to which the B16 melanoma cells expressing the human Eva1 protein were administered, and from day 1 thereafter the B2E5-48 mouse antibody was administered. In the figure, the vertical axis represents an average number of colonies formed in the lungs of one mouse in each antibody administration group (regarding the representations in the figure, the same shall apply also to FIGS. 18, 20, and 24).
Figure 17:
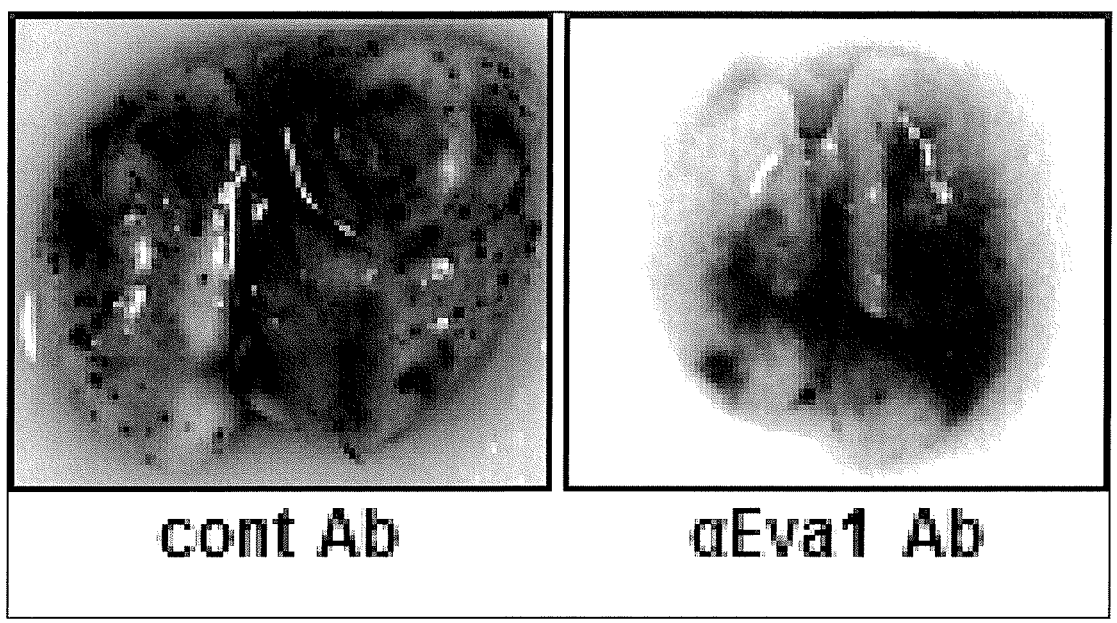
FIG. 17 shows photographs for illustrating the result of observing melanoma colonies formed in lungs of mice to which B16 melanoma cells were administered, and from day 1 thereafter the B2E5-48 mouse antibody was administered. In the figure, the result of administering the B2E5-48 mouse antibody is shown on the right side, and the result of administering not the antibody but an isotype control antibody thereof is shown on the left side.

(1) The B16-Eva1 in an amount of $1\times10^5$ cells were administered into the caudal veins of 5- to 8-week old C57BL/6 mice. From day 1 after the melanoma inoculation, 100 μg of the B2E5-48 mouse antibody was administered into the caudal veins at intervals of 3 days four times in total. Then, on day 13 after the melanoma inoculation, the lungs were collected, and the number of melanoma colonies thus formed was counted (n=5). FIGS. 15 and 16 show the obtained result.

(2) The B16-GFP in an amount of $1\times10^5$ cells were administered into the caudal veins of 5- to 8-week old C57BL/6 mice. From day 1 after the melanoma inoculation, 100 μg of the B2E5-48 mouse antibody or the B2E5-48 chimeric antibody was administered into the caudal veins at intervals of 3 days four times in total. Then, on day 13 after the melanoma inoculation, the lungs were collected, and the number of melanoma colonies thus formed was counted (n=5). FIGS. 17 to 20 show the obtained result.

Figure 21:
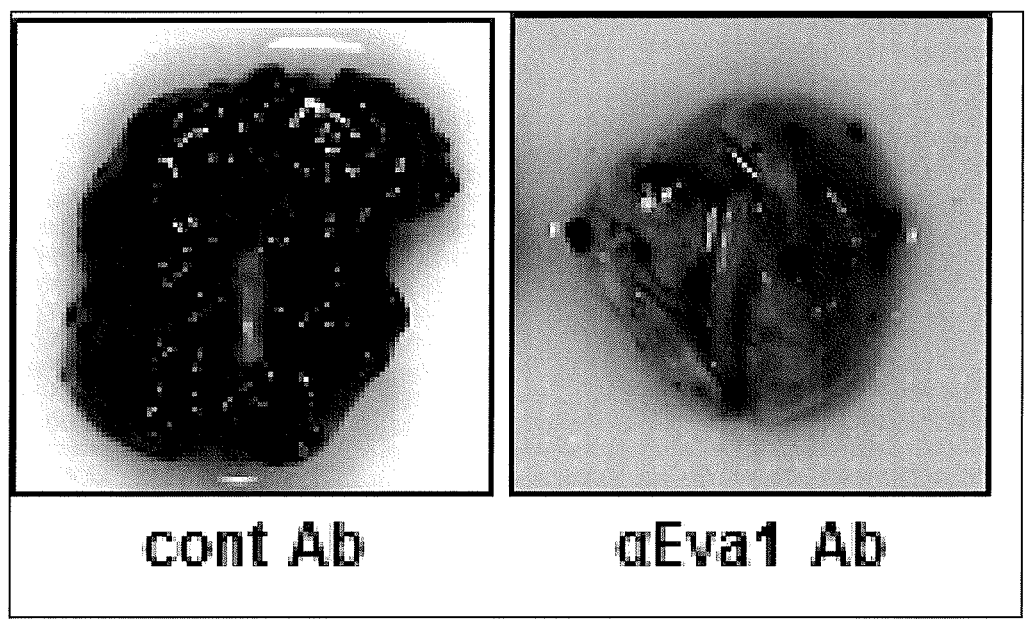
FIG. 21 shows photographs for illustrating the result of observing melanoma colonies formed in lungs of mice to which the B16 melanoma cells were administered, and from day 14 thereafter the B2E5-48 mouse antibody was administered. In the figure, the result of administering the B2E5-48 mouse antibody is shown on the right side, and the result of administering not the antibody but an isotype control antibody thereof is shown on the left side.
Figure 22:
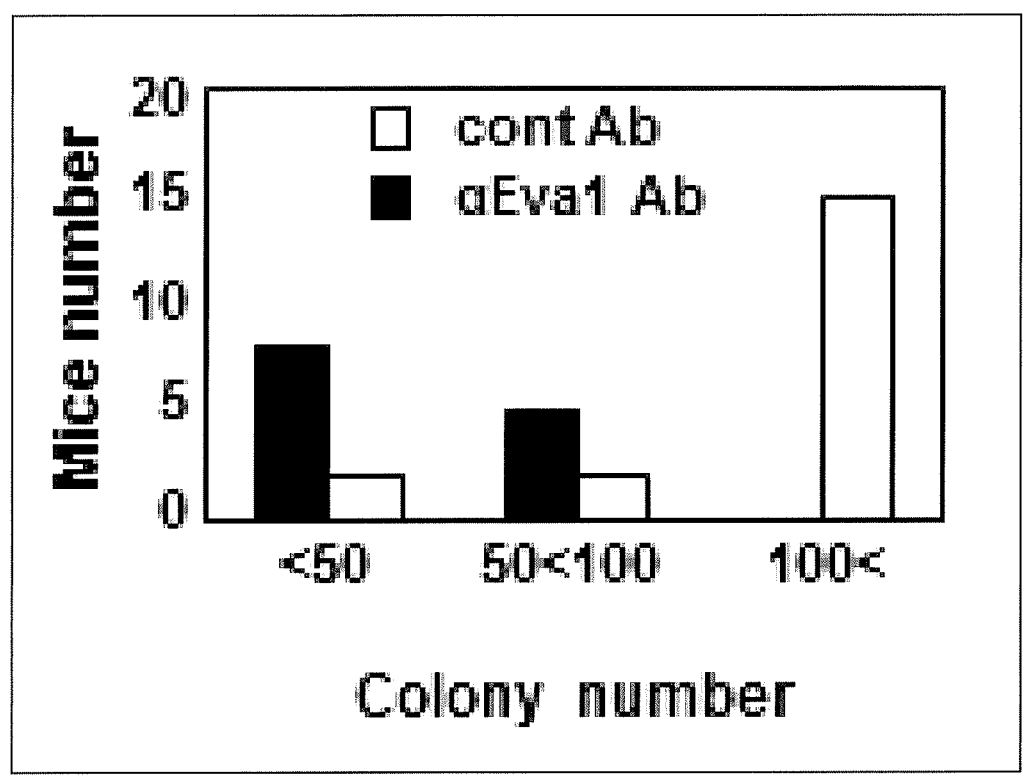
FIG. 22 is a graph showing the result of counting the number of melanoma colonies formed in the lungs of the mice to which the B16 melanoma cells were administered, and from day 14 thereafter the B2E5-48 mouse antibody was administered. In the figure, the horizontal axis represents the number of colonies formed in the lungs (less than 50 colonies, 50 colonies or more to less than 100 colonies, 100 colonies or more, in this order from the left), and the vertical axis represents the number of antibody mice each of which was classified according to the number of colonies formed.

(3) The B16-GFP in an amount of $1\times10^5$ cells were administered into the caudal veins of 5- to 8-week old C57BL/6 mice. From day 13 after the melanoma inoculation, 100 μg of the B2E5-48 mouse antibody was administered into the caudal veins at intervals of 3 days three times in total. Then, on day 22 after the melanoma inoculation, the lungs were collected, and the number of melanoma colonies thus formed was counted (n=5). Moreover, according to the number of colonies formed, the mice were grouped, and the number of mice in each group was also counted. FIGS. 21 and 22 show the obtained result.

(4) The B16-Eva1 in an amount of $1\times10^5$ cells were administered into the caudal veins of 5- to 8-week old C57BL/6 mice. From day 1 after the melanoma inoculation, 100 μg of the C3 mouse antibody was administered into the caudal veins at intervals of 4 days four times in total. Then, on day 14 after the melanoma inoculation, the lungs were collected, and the number of melanoma colonies thus formed was counted (n=5).

Figure 23:
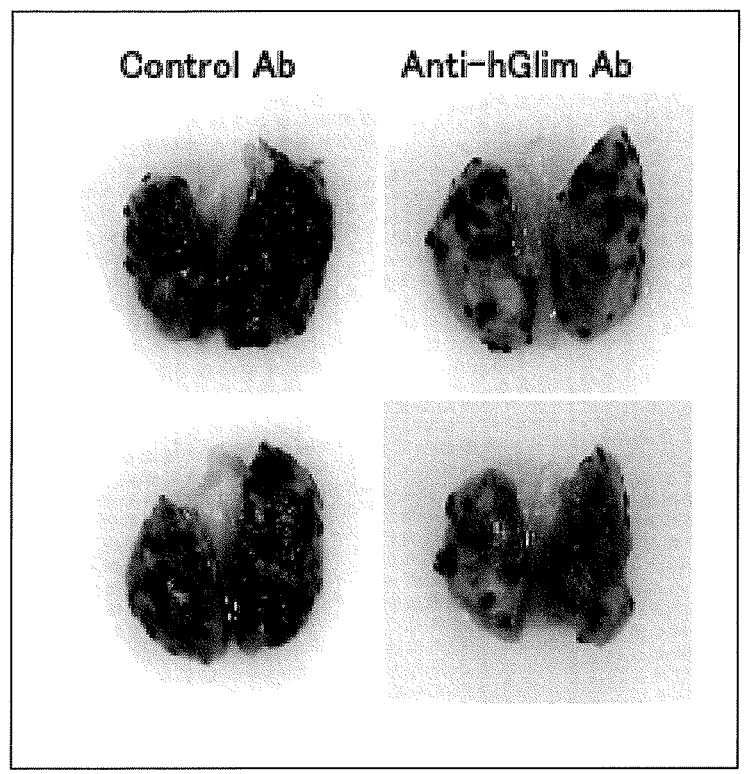
FIG. 23 shows photographs for illustrating the result of observing melanoma colonies formed in lungs of mice to which the B16 melanoma cells expressing the human Eva1 protein were administered, and from day 1 thereafter the C3 mouse antibody was administered. In the figure, the results of administering the C3 mouse antibody (two examples) are shown on the right side, and the results of administering not the antibody but an isotype control antibody thereof (two examples) are shown on the left side.
Figure 24:
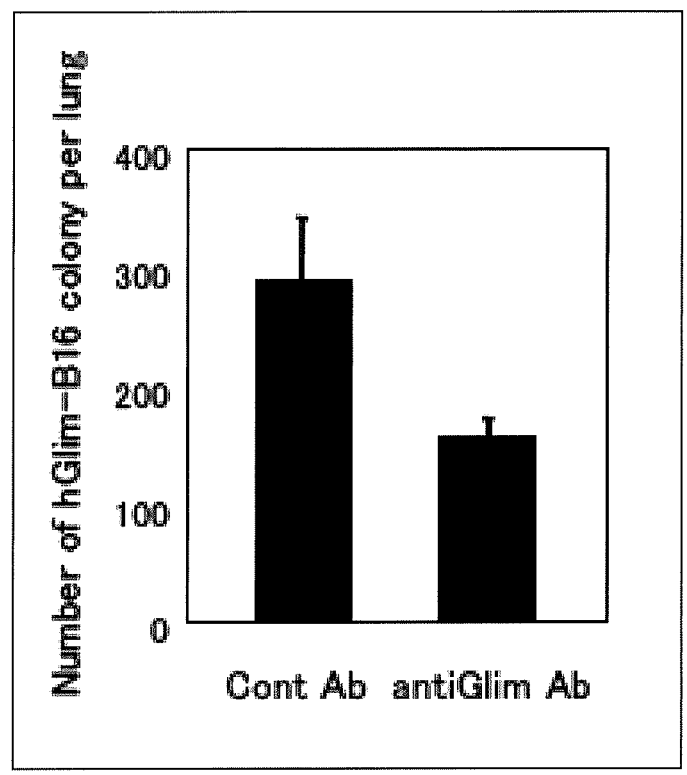
FIG. 24 is a graph showing the result of counting the number of melanoma colonies formed in the lungs of the mice to which the B16 melanoma cells expressing the human Eva1 protein were administered, and from day 1 thereafter the C3 mouse antibody was administered.

FIGS. 23 and 24 show the obtained result.

(5) The B16-GFP in an amount of $1\times10^5$ cells were administered into the caudal veins of 5- to 8-week old C57BL/6 mice. From day 1 after the melanoma inoculation, 100 μg of the C3 mouse antibody was administered into the caudal veins at intervals of 4 days four times in total. Then, on day 14 after the melanoma inoculation, the lungs were collected, and the number of melanoma colonies thus formed was counted (n=5).

FIGS. 23 and 24 show the obtained result.

Note that the number of colonies was counted according to the method described in Nakamura K. et al, Life Sciences, 2002, vol. 70, pp. 791 to 798. In addition, in any analysis, an isotype-control-antibody administration group was prepared as a control group. Further, the obtained result was analyzed by Student's t-test using software EXCEL manufactured by Microsoft Corporation to calculate the P value, and the significance of the difference from the control group was evaluated.

As shown in FIGS. 15 and 16, it was revealed that, in the mice to which the B2E5-48 mouse antibody was administered, the colony formation in the lungs by the B16 melanoma cells forced to express the Eva1 protein was successfully suppressed to great extent. Moreover, this result resulted from the antibody administration from day 1 after the melanoma inoculation. From this point, it is suggested that the B2E5-48 mouse antibody exhibited a prophylactic effect against cancer metastasis.

As described above, B16 melanoma cells do not express the Eva1 protein under the culturing conditions. However, as apparent from the results shown in FIGS. 17 to 20, the colony formation in the lungs by the B16 melanoma cells not forced to express such an Eva1 protein was also suppressed by the B2E5-48 mouse antibody and the B2E5-48 chimeric antibody to great extent.

Accordingly, lungs of mice inoculated with B16 melanoma cells were analyzed by the flow cytometry using an anti-Eva1 polyclonal antibody, and the presence or absence of the Eva1 protein in the cells was checked. Although unillustrated, the result revealed that the Eva1 protein was expressed in the B16 melanoma cells having metastasized to the lungs. Thus, it is suggested that the anti-tumor effect of the B2E5-48 antibody observed against the B16 melanoma cells was exhibited through the Eva1 protein expression which occurred after the administration into the mouse bodies.

Figure 18:
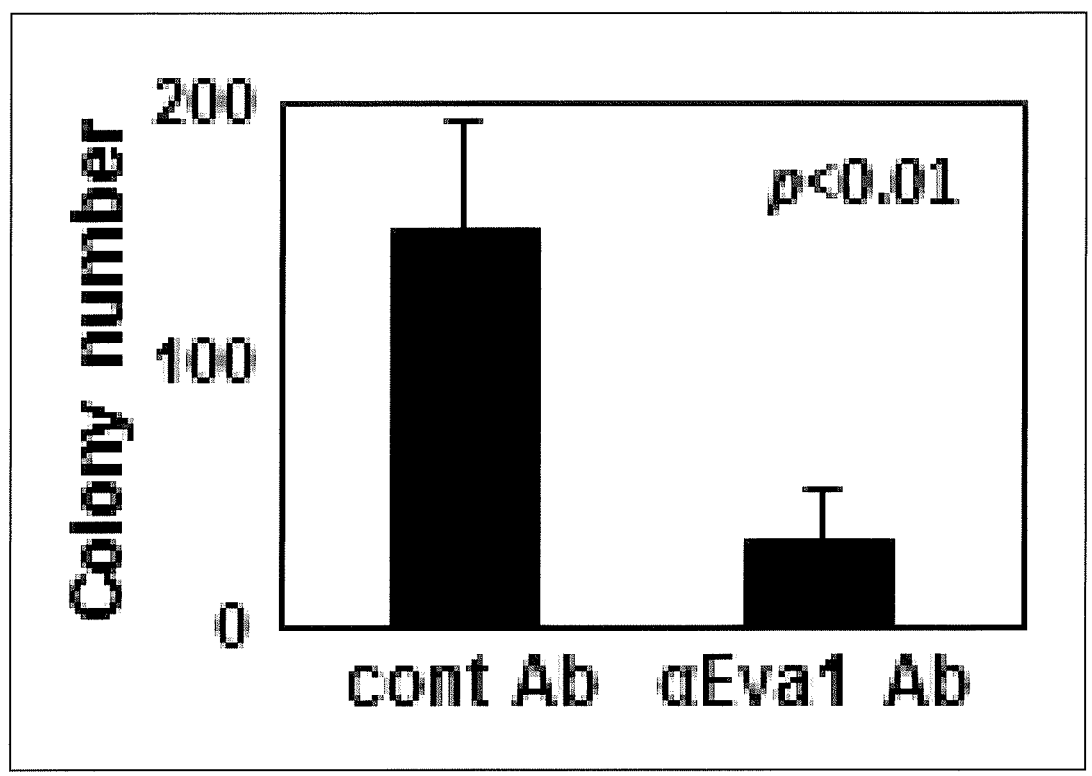
FIG. 18 is a graph showing the result of counting the number of melanoma colonies formed in the lungs of the mice to which the B16 melanoma cells were administered, and from day 1 thereafter the B2E5-48 mouse antibody was administered.
Figure 19:
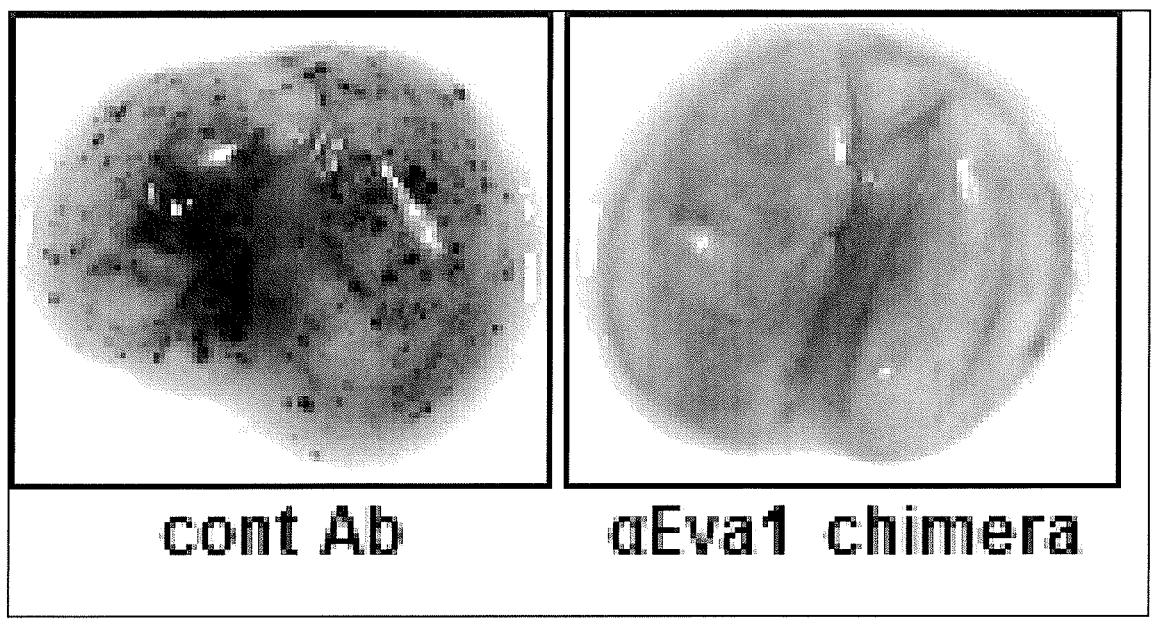
FIG. 19 shows photographs for illustrating the result of observing melanoma colonies formed in lungs of mice to which the B16 melanoma cells were administered, and from day 1 thereafter the B2E5-48 chimeric antibody was administered. In the figure, the result of administering the B2E5-48 chimeric antibody is shown on the right side, and the result of administering not the antibody but an isotype control antibody thereof is shown on the left side.
Figure 20:
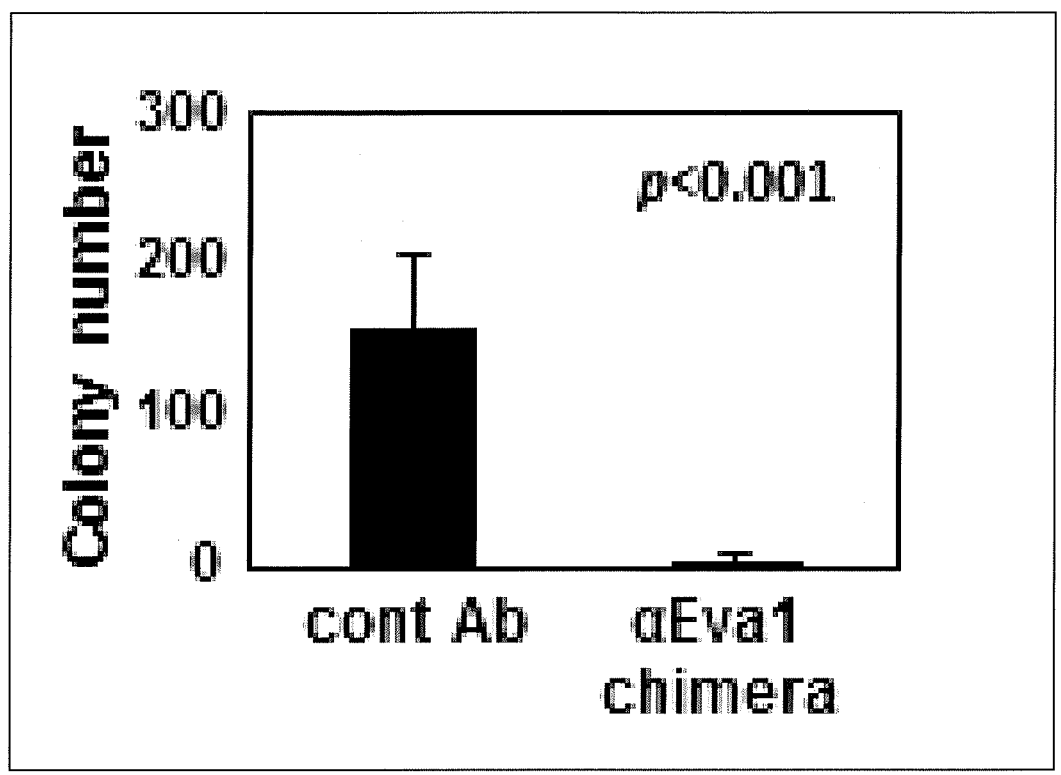
FIG. 20 is a graph showing the result of counting the number of melanoma colonies formed in the lungs of the mice to which the B16 melanoma cells were administered, and from day 1 thereafter the B2E5-48 chimeric antibody was administered.

Meanwhile, it was also revealed as shown in FIGS. 18 and 20 that the anti-tumor effect against the B16 melanoma cells was improved by the chimerization of the B2E5-48 antibody.

Further, it was revealed as shown in FIGS. 21 and 22 that even when the timing of starting the antibody administration after the B16 melanoma cell inoculation was delayed from day 1 to day 14 after the inoculation, the colony formation in the lungs by the B16 melanoma cells was successfully suppressed to great extent in the mice to which the B2E5-48 mouse antibody was administered. Moreover, this result resulted from the antibody administration given even after 14 days elapsed from the melanoma inoculation. From this point, it is suggested that the B2E5-48 mouse antibody exhibited a therapeutic effect against metastasized cancer.

Furthermore, as apparent from the results shown in FIGS. 23 and 24, like the B2E5-48 mouse antibody, an in vivo anti-tumor activity was observed also from the C3 mouse antibody.

INDUSTRIAL APPLICABILITY

As has been described above, the antibody of the present invention exhibits a high affinity for a human-derived Eva1 protein and has high ADCC and/or CDC activities. Further, the antibody of the present invention exhibits a high anti-tumor activity in vivo, too. Thus, the antibody of the present invention is useful as a drug for cancer treatment or prevention, a drug for cancer metastasis suppression, and the like.

In addition, the present invention is not limited at all to the above descriptions of the embodiments and Examples of the invention. This invention also includes various modifications those skilled in the art can arrive at without departing from the scope of claims. The entire contents of the papers, patent application publications, and so forth cited herein are incorporated by reference herein for all purposes.

SEQUENCE LISTING FREE TEXT

SEQ ID NO: 1
<223> Signal peptide and Variable Region of Light Chain (B2E5-48)
SEQ ID NO: 3
<223> Variable Region of Light Chain (B2E5-48)
SEQ ID NO: 4
<223> CDR1 of Light Chain (B2E5-48)
SEQ ID NO: 5
<223> CDR2 of Light Chain (B2E5-48)
SEQ ID NO: 6
<223> CDR3 of Light Chain (B2E5-48)
SEQ ID NO: 7
<223> Signal peptide and Variable Region of Heavy Chain (B2E5-48)
SEQ ID NO: 9
<223> Variable Region of Heavy Chain (B2E5-48)
SEQ ID NO: 10
<223> CDR1 of Heavy Chain (B2E5-48)
SEQ ID NO: 11
<223> CDR2 of Heavy Chain (B2E5-48)
SEQ ID NO: 12
<223> CDR3 of Heavy Chain (B2E5-48)
SEQ ID NO: 13
<223> Signal peptide and Variable Region of Light Chain (C3)
SEQ ID NO: 15
<223> Variable Region of Light Chain (C3)
SEQ ID NO: 16
<223> CDR1 of Light Chain (C3)
SEQ ID NO: 17
<223> CDR2 of Light Chain (C3)
SEQ ID NO: 18
<223> CDR3 of Light Chain (C3)
SEQ ID NO: 19
<223> Signal peptide and Variable Region of Heavy Chain (C3)
SEQ ID NO: 21
<223> Variable Region of Heavy Chain (C3)
SEQ ID NO: 22
<223> CDR1 of Heavy Chain (C3)
SEQ ID NO: 23
<223> CDR2 of Heavy Chain (C3)
SEQ ID NO: 24
<223> CDR3 of Heavy Chain (C3)
SEQ ID NO: 25
<223> Variable Region of Light Chain (A5D11-10)
SEQ ID NO: 27
<223> CDR1 of Light Chain (A5D11-10)
SEQ ID NO: 28
<223> CDR2 of Light Chain (A5D11-10)
SEQ ID NO: 29
<223> CDR3 of Light Chain (A5D11-10)
SEQ ID NO: 30
<223> Variable Region of Heavy Chain (A5D11-10)
SEQ ID NO: 32
<223> CDR1 of Heavy Chain (A5D11-10)
SEQ ID NO: 33
<223> CDR2 of Heavy Chain (A5D11-10)
SEQ ID NO: 34
<223> CDR3 of Heavy Chain (A5D11-10)
SEQ ID NO: 35
<223> hEva1
SEQ ID NO: 37
<223> mEva1

The invention claimed is:

1. An anti-Eva1 antibody molecule, wherein said antibody molecule is an antibody molecule comprising:
   a light chain variable region comprising light chain complementarity-determining regions (CDRs) 1-3, and
   a heavy chain variable region comprising heavy chain CDRs 1-3, and wherein
   said light chain CDRs 1-3 comprise the amino acid sequences of SEQ ID NOs: 4 to 6, respectively, and
   said heavy chain CDRs 1-3 comprise the amino acid sequences of SEQ ID NOs: 10 to 12, respectively.

2. The antibody molecule according to claim 1, wherein said antibody molecule comprises a human constant region.

3. The antibody molecule according to claim 1, wherein said antibody molecule has at least one cytotoxicity activity selected from the group consisting of antibody-dependent cell-mediated cytotoxicity (ADCC) and complement-dependent cytotoxicity (CDC).

4. A pharmaceutical composition comprising the antibody molecule according to claim 1 as an active ingredient, and further comprising a pharmaceutically acceptable carrier or a pharmaceutically acceptable medium.

* * * * *